(12) United States Patent
Makoto et al.

(10) Patent No.: US 9,717,816 B2
(45) Date of Patent: Aug. 1, 2017

(54) DEODORIZATION AND STERILIZATION APPARATUS AND METHOD

(75) Inventors: Miyamoto Makoto, Kanagawa (JP); Takenoshita Kazutoshi, Kanagawa (JP); Kumagai Yuuki, Kanagawa (JP); Nakayama Yoko, Kanagawa (JP)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 963 days.

(21) Appl. No.: 13/312,236

(22) Filed: Dec. 6, 2011

(65) Prior Publication Data

US 2012/0148445 A1 Jun. 14, 2012

(30) Foreign Application Priority Data

Dec. 10, 2010 (JP) ................... 2010-275509

(51) Int. Cl.
*F24F 3/16* (2006.01)
*A61L 9/22* (2006.01)
*H05H 1/24* (2006.01)

(52) U.S. Cl.
CPC ......... *A61L 9/22* (2013.01); *F24F 3/16* (2013.01); *H05H 1/2406* (2013.01); *F24F 2003/1664* (2013.01); *F24F 2003/1689* (2013.01); *H05H 2001/2412* (2013.01); *H05H 2245/1225* (2013.01)

(58) Field of Classification Search
CPC ................. A61L 9/16; A61L 9/22; F24F 3/16
USPC .................................... 422/5, 186
See application file for complete search history.

(56) References Cited

U.S. PATENT DOCUMENTS 3,798,879 A * 3/1974 Schmidt-Burbach ... B03C 3/155
55/302
2004/0140194 A1* 7/2004 Taylor et al. ................. 204/164

FOREIGN PATENT DOCUMENTS

| EP | 1258281 | 11/2002 |
| EP | 1782843 | 5/2007 |
| EP | 2042197 | 4/2009 |
| EP | 2128550 | 12/2009 |
| FR | 2921867 | * 4/2009 |
| WO | 2006/065491 | 6/2006 |
| WO | WO 2009/053577 A1 * | 4/2009 |

OTHER PUBLICATIONS

Derwent Abstract for FR 2921867; published Apr. 2009.*

(Continued)

*Primary Examiner* — Sean E Conley
(74) *Attorney, Agent, or Firm* — Staas & Halsey LLP

(57) ABSTRACT

A deodorization and sterilization apparatus and method, which increases an amount of generated active species and collects floating bacteria or odor materials in air at one place, such that the active species make contact with the collected floating bacteria or odor materials to achieve high-efficiency sterilization and deodorization. A pair of electrodes is provided, plasma discharge is carried out by applying designated voltage between the pair of electrodes, fluid passage holes are provided at corresponding parts of respective electrodes so as to communicate with each other, and at least one absorption member to absorb floating bacteria or odor materials is disposed at the downstream of a fluid passing through the fluid passage holes.

15 Claims, 22 Drawing Sheets

(56) References Cited

OTHER PUBLICATIONS

English language machine translation of WO 2009/053577 A1; published Apr. 2009.*
Partial European Search Report dated Mar. 28, 2012 issued in corresponding European Patent Application No. 11191821.5.
Japanese Decision of Refusal dated Mar. 5, 2015 from Japanese Patent Application No. 2010-275509, 2 pages.
European Office Action dated Dec. 21, 2016 in corresponding European Patent Application No. 11 191 821.5, 5 pages.

* cited by examiner

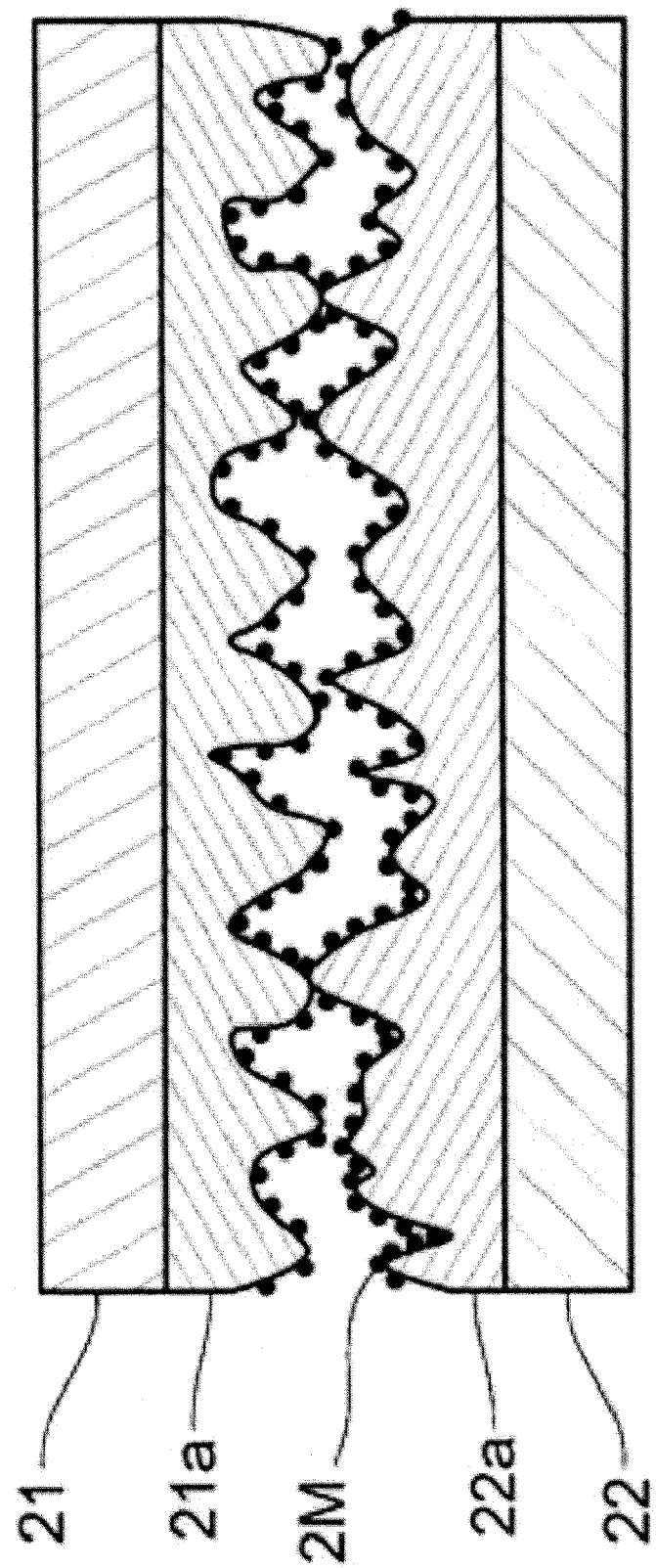

DEODORIZATION AND STERILIZATION APPARATUS AND METHOD

CROSS-REFERENCE TO RELATED APPLICATIONS

This application claims the priority benefit of Japanese Patent Application No. 2010-275509, filed on Dec. 10, 2010 in the Japanese Patent Office, the disclosure of which is incorporated herein by reference.

BACKGROUND

1. Field

Example embodiments of the following description relate to a deodorization and sterilization apparatus and method, and more particularly, a deodorization and sterilization apparatus and method, which increases an amount of generated active species and collects floating bacteria or odor materials in air at one place, such that the active species make contact with the collected floating bacteria or odor materials to achieve high-efficiency sterilization and deodorization.

2. Description of the Related Art

Recently, the requirements of air quality control in living environments, such as sterilization or deodorization, have become more stringent due to the increase in persons suffering from atopy, asthma and allergies, and the increase in the risk of infectious diseases represented as explosive spread of new types of influenza. Further, as society becomes increasingly affluent, an amount of storage food increases or an opportunity to store leftovers increases, and thus, importance of controlling an environment in storage equipment, such as a refrigerator, increases.

In order to control air quality in living environments, physical control generally using a filter was conventionally executed. Through physical control, relatively large dust floating in air and/or bacteria or viruses may be trapped according to sizes of filter holes. Further, activated carbon having numerous absorption sites may trap odorous molecules. However, since, in order to trap such substances, air in a space of a target object to be controlled needs to completely pass through the filter, an apparatus needs to be large, maintenance cost required to replace the filter is increased, and the apparatus has no effect upon attached particles. Therefore, in order to achieve sterilization and deodorization of the attached particles, chemically active species may be discharged to a space desired to be sterilized or deodorized. When a medicine is distributed or an aromatic or a deodorizer is discharged, active species need to be prepared in advance and periodic supplement of the active species is indispensable. On the other hand, units which generate plasma in the atmosphere and attempt sterilization and deodorization using chemical active species generated due to plasma generation have recently been increasingly proposed.

Technology for generating plasma in the atmosphere through discharge and achieving sterilization and deodorization by ions or radicals (hereinafter, referred to as active species) generated thereby, may be classified into two types described below:

(1) A passive plasma generation apparatus which causes bacteria or viruses floating within the atmosphere (hereinafter, referred to as floating bacteria) or odorous materials (hereinafter, referred to as odors) to react with active species within a restricted volume in the apparatus (for example, Japanese Patent Laid-open Publication No. 2002-224211)

(2) An active plasma generation apparatus which discharges active species generated by a plasma generation unit into a closed space (for example, a living room, a bath room, the inside of a car, etc) having a larger volume than the passive plasma generation apparatus and causes the discharged active species to react with floating bacteria or odors due to collision with the floating bacteria or odors in the atmosphere (for example, Japanese Patent Laid-open Publication No. 2003-79714).

The passive plasma generation apparatus may be advantageous in that high sterilization and deodorization effects are expected through generation of active species of a high concentration due to generation of plasma in a small volume. However, the passive plasma generation apparatus may be disadvantageous in that the floating bacteria or odors need to be introduced into the apparatus, and thus, the size of the apparatus is increased, ozone as a byproduct due to plasma generation is generated, and separate installation of a filter to absorb or decompose ozone to prevent ozone from leaking to the outside of the apparatus is required.

Further, the active plasma generation apparatus may be advantageous in that the size of the apparatus is relatively decreased and sterilization of bacteria attached to the surfaces of clothes or household goods (hereinafter, referred to as attached bacteria) or decomposition of odors absorbed to the surfaces is expected, in addition to sterilization of floating bacteria or decomposition of odors in air. However, the active plasma generation apparatus may be disadvantageous in that the concentration of active species is decreased due to diffusion of the active species into a considerably large closed space as compared with the volume of the apparatus, and thus, sterilization and deodorization are expected only upon active species having a long life. Consequently, deodorization effects are scarcely expected in a space having a high concentration of odors (concentration 10,000 times greater than the concentration of the active species).

As described above, the passive plasma generation apparatus exhibits effects restricted to floating bacteria or odors contained in an air flow introduced into the apparatus, and the active plasma generation apparatus exhibits effects only upon floating bacteria, attached bacteria and odors having a low concentration. That is, the conventional plasma generation apparatuses may achieve either sterilization of floating bacteria and deodorization, or sterilization of floating bacteria and attached bacteria having a low concentration and deodorization of attached odors having a low concentration.

However, there are several situations in daily life in which both sterilization of attached bacteria and deodorization of odors of a high concentration are desired to be simultaneously achieved. Typically, within a refrigerating chamber of a refrigerator, bacteria attached to the surfaces of foods or storage containers are present, and odors generated from foods and remaining food waste are present.

SUMMARY

The foregoing and/or other aspects are achieved by providing a deodorization and sterilization apparatus and method, which increases an amount of generated active species and collects floating bacteria or odor materials in air at one place, such that the active species make contact with the collected floating bacteria or odor materials to achieve high-efficiency sterilization and deodorization.

The foregoing and/or other aspects are achieved by a deodorization and sterilization apparatus, which includes a pair of electrodes, plasma discharge being carried out by applying designated voltage between the pair of electrodes, wherein fluid passage holes are provided at corresponding parts of respective electrodes so as to communicate with each other, and at least one absorption member to absorb floating bacteria or odor materials is disposed at the downstream of a fluid passing through the fluid passage holes. In this case, the corresponding parts mean that the respective fluid holes formed on the electrodes are located at the same positions as seen from the plane directions of the electrodes, and are located at approximately the same x and y coordinate positions of the electrodes as the pair of electrodes on an x-y plane is observed in the z axis direction in a rectangular coordinate system.

Through the above configuration, a contact area between plasma generated from the respective fluid passage holes and the fluid may be increased, thereby increasing an amount of generated active species. Further, since the absorption member is disposed at the downstream of the fluid passage holes, even if air having passed through the fluid passage holes includes floating bacteria which are not non-activated or odor materials which are not decomposed, the floating bacteria and the odor materials may be collected at one place through absorption via the absorption member, and thus, high-efficiency sterilization and deodorization of the floating bacteria and the odor materials may be achieved by contact of the active species with the absorption member.

In order to sufficiently obtain sterilization of the floating bacteria absorbed by the absorption member and deodorization of the odor materials absorbed by the absorption member, an air ion number density on the surface of the absorption member or around the surface of the absorption member is approximately $10,000/cm^3$ or more.

Through the above configuration, if an air current is generated in the atmosphere in which the deodorization and sterilization apparatus is installed, the absorption member may be installed in the direction of the air current. On the other hand, if a sufficient air current is not present in the atmosphere, in order to allow the active species generated by the plasma, which is generated by the fluid passage holes or a region around the fluid passage holes, to effectively contact the absorption member, the deodorization and sterilization apparatus may further include an air blowing device to forcibly blow air toward the fluid passage holes and to generate an air current from the fluid passage holes toward the absorption member.

In order to achieve sterilization or deodorization of bacteria or odor materials attached to surrounding walls instead of the absorption member, the air blowing device may forcibly blow air in a direction opposite to the fluid passage holes and generate an air current from the fluid passage holes in a direction opposite to the absorption member.

In order to allow air having passed through the fluid passage holes to effectively contact the absorption member, the absorption member may include a plurality of through holes formed in the air blowing direction. If through holes are not formed on the absorption member, ventilation is low and pressure loss is high, and thus an amount of air blown by the air blowing device is reduced. On the other hand, if the absorption member includes through holes, a sufficient amount of air blown by the air blowing device may be obtained and effective reaction with the surface of the absorption member may be obtained. Further, a reaction state on the surface of the absorption member serving as a deodorization and sterilization field may be indirectly detected by analyzing air having passed through the through holes. Therefore, a sensor may be provided at the downstream of the through holes to detect a progress state of deodorization or a state representing lowering of an absorbing capacity, thus increasing an amount of generated active species, promoting decomposition due to an external subsidiary factor, such as, ultraviolet rays or a light source, or achieving feedback control.

The absorption member may include an absorbent formed of silica gel, activated carbon, zeolite, mesoporous silica, or combinations thereof. Further, the absorption member may be coated or impregnated with various materials. For example, as to such materials, fine particles of photocatalysts, such as titanium oxide and manganese oxide, metal complexes, and precious metals, such as platinum, palladium, rhodium, etc., may be considered. Of course, these materials may be mixed. By impregnating the absorption member with these materials, sterilization or deodorization performance may be further improved. Here, the absorption member may be formed by retaining an absorbent on a mesh-type base.

If a conventional plasma generation apparatus requiring high voltage is applied to a refrigerator using a combustible gas instead of Freon gas, safety may be lowered. The used combustible gas may leak into the refrigerator, and sparks causing high voltage which are generated in the above atmosphere may ignite and cause an explosion accident. Therefore, the deodorization and sterilization apparatus may further include an explosion proof device, including protective covers disposed at the outside of the pair of the electrodes to prevent flames generated from the combustible gas introduced into the fluid passage holes by the plasma from propagating to the outside over the protective covers. In this case, in order to effectively use the configuration of the explosion proof device, the absorbent may be disposed on the protective covers.

In order to obtain safety without lowering deodorizing and sterilizing capacities, each of the protective covers may include a metal mesh disposed at the outside of the pair of the electrodes, and the metal mesh may have a wire diameter of approximately 1.5 mm or less and an aperture ratio of approximately 30% or more.

The odor materials may be divided into materials having a large molecule diameter and materials having a small molecule diameter. For example, as representative odor materials, the molecule diameter of methylmercaptan is about 0.18 nm and the molecule diameter of trimethylamine is about 0.30 nm, i.e., twice the molecule diameter of methylmercaptan. Further, terpenes having a large molecular volume have a molecule diameter of about 1 nm. In order to absorb these odor materials including odor molecules having various sizes, plural kinds of absorbents having different absorption characteristics due to a difference of particular pore sizes may be provided. In this case, a plurality of absorption members having different absorption characteristics is provided. Further, odor materials or floating bacteria have different affinities to the absorbents, according to these molecular characteristics or surface characteristics. In this case, hydrophilic and hydrophobic properties of the surfaces of the absorbents may be controlled, or polarity charging potentials or charge amounts may be controlled, according to characteristics of the odor materials and the floating bacteria.

In order to increase the number of the active species contained in the fluid, having passed through the fluid passage holes, and to suppress concentration of generated ozone, voltage in a pulse mode may be applied to the respective electrodes and have a peak value within the range of approximately 100V to 5,000V and a pulse width in the range of approximately 0.1 μs to 300 μs.

It is expected that kinds of active species optimal to decompose odor materials absorbed to the absorption member or floating bacteria are different. Therefore, increase of generation of active species most greatly contributing to deodorization or increase of generation of active species most greatly contributing to sterilization by controlling the polarity or amount of ions is effective in increase in deodorization efficiency and a sterilization rate. Therefore, DC bias voltage in the range of approximately −500V to +500V may be applied to the voltage applied to the respective electrodes.

In order to enable decomposition of high-concentration odors by causing air to pass through deodorization fields formed in the fluid passage holes, as well as, to decompose the floating bacteria and odor materials absorbed to the absorption member, a plurality of fluid passage holes, corresponding to the pair of electrodes may be provided, a path formation member forming a path to communicate the plurality of fluid passage holes with each other may be provided, air may pass through the plurality of communicating fluid passage holes, a fluid passage hole at one end of the path formed by the path formation member may face the upstream in the air blowing direction and another fluid passage hole at the other end of the path formed by the path formation member may face the absorption member.

An introduction path formation member to guide active species generated via the fluid passage holes to the absorption member may be disposed between the fluid passage holes and the absorption member, and the introduction path formation member has a retaining structure to retain the active species. Floating bacteria, odor materials and active species generated by the plasma electrode unit may be retained in the retaining structure, and thus, the introduction path formation member having the retaining structure may have a long reaction time, as compared with a rectilinear path without a retaining part, thereby increasing sterilization and deodorization efficiency.

In order to reduce power consumption during operation of the deodorization and sterilization apparatus, an absorption mode in which application of voltage to the plasma electrode unit is stopped to allow the absorption member to absorb floating bacteria or odor materials, and a decomposition mode in which voltage is applied to the plasma electrode unit after the absorption mode to supply active species generated by plasma to the absorption member, may be used.

Additional aspects, features, and/or advantages of example embodiments will be set forth in part in the description which follows and, in part, will be apparent from the description, or may be learned by practice of the disclosure.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 5 is an enlarged cross-sectional view illustrating the configuration of opposite surfaces of the electrode unit, according to example embodiments;

DETAILED DESCRIPTION

Figure 1:
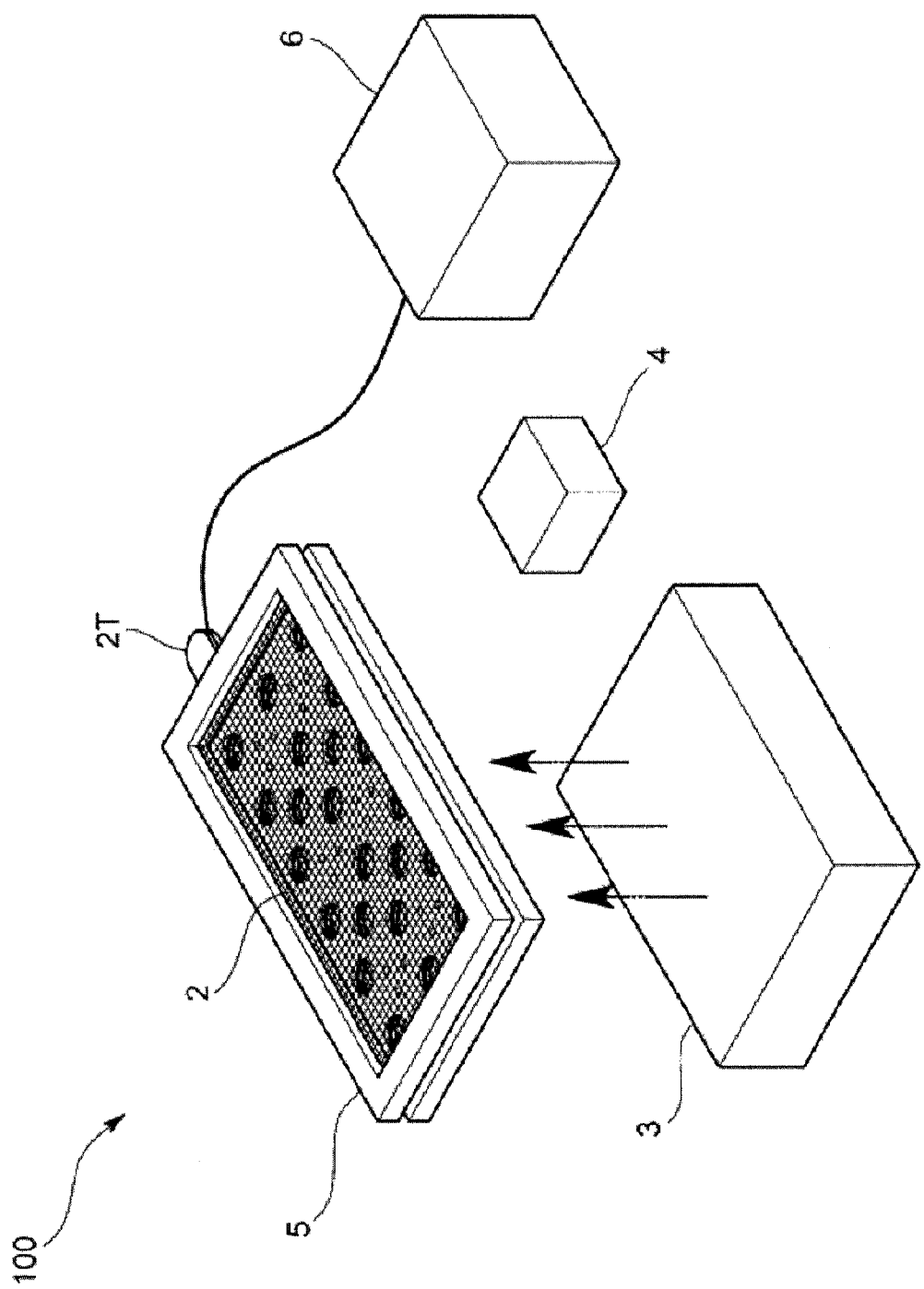
FIG. 1 is a perspective view illustrating a deodorization and sterilization apparatus in accordance with one embodiment of the present disclosure.

Reference will now be made in detail to the embodiments of the present disclosure, examples of which are illustrated in the accompanying drawings, wherein like reference numerals refer to like elements throughout.

A deodorization and sterilization apparatus 100 in accordance with one embodiment of the present disclosure is used in a home appliance, for example, a refrigerator, a washing machine, a laundry dryer, a cleaner, an air conditioner or an air cleaner, and is employed to achieve deodorization of air at the inside or outside of the home appliance or sterilization of floating bacteria or attached bacteria at the inside or outside of the home appliance and deodorization of odor materials.

Figure 2:
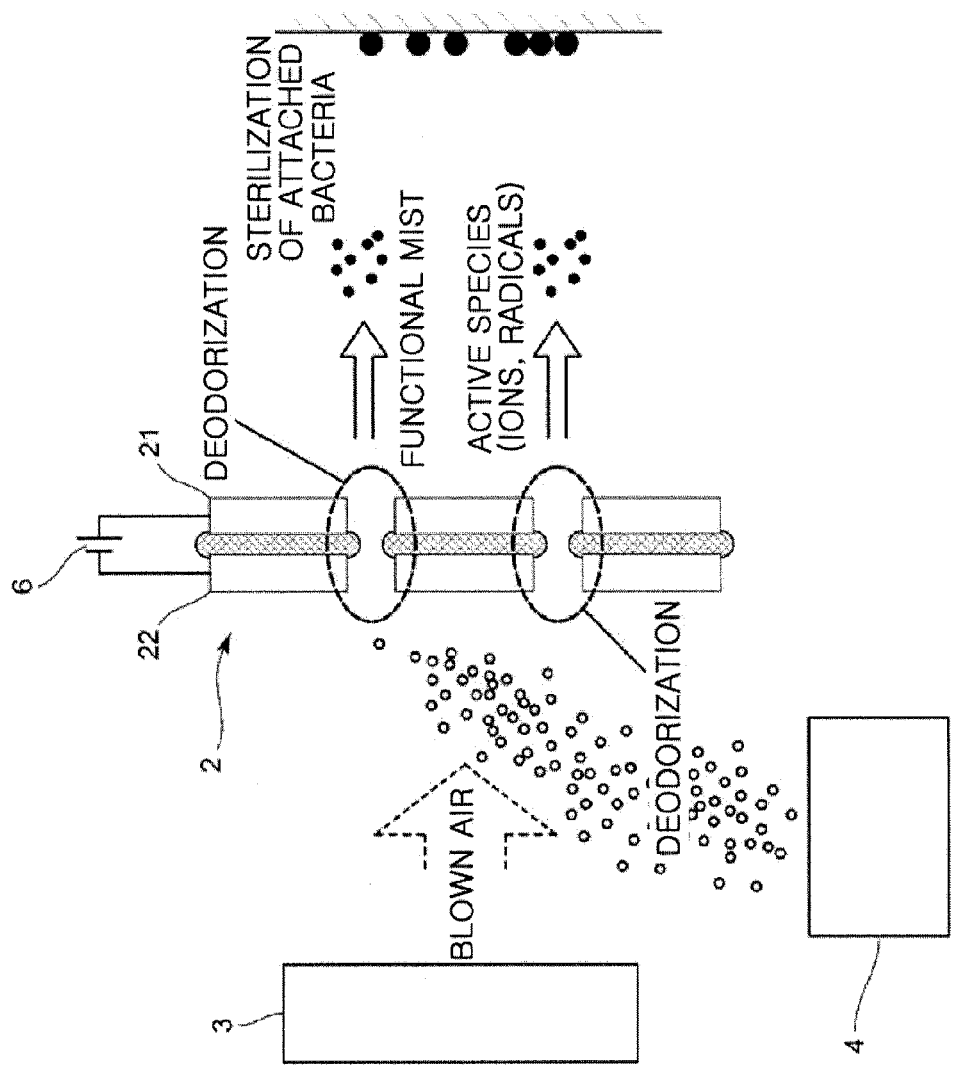
FIG. 2 is a schematic view illustrating operation of the deodorization and sterilization apparatus, according to example embodiments.

In more detail, as shown in FIGS. 1 and 2, the deodorization and sterilization apparatus 100 includes a plasma electrode unit 2 to generate active species, such as ions or radicals, through micro gap plasma, an air blowing device 3 provided at the outside of the plasma electrode unit 2 to forcibly blow air (an air current) to the plasma electrode unit 2, an absorption member 4 installed at a side of the plasma electrode unit 2 opposite to the air blowing device 3 to absorb floating bacteria or odor materials, an explosion proof device 5 provided at the outside of the plasma electrode unit 2 to prevent flames generated by the plasma electrode unit 2 from propagating to the outside, and a power supply 6 to apply high voltage to the plasma electrode unit 2.

Hereinafter, the respective components 2-6 will be described with reference to the accompanying drawings.

Figure 3:
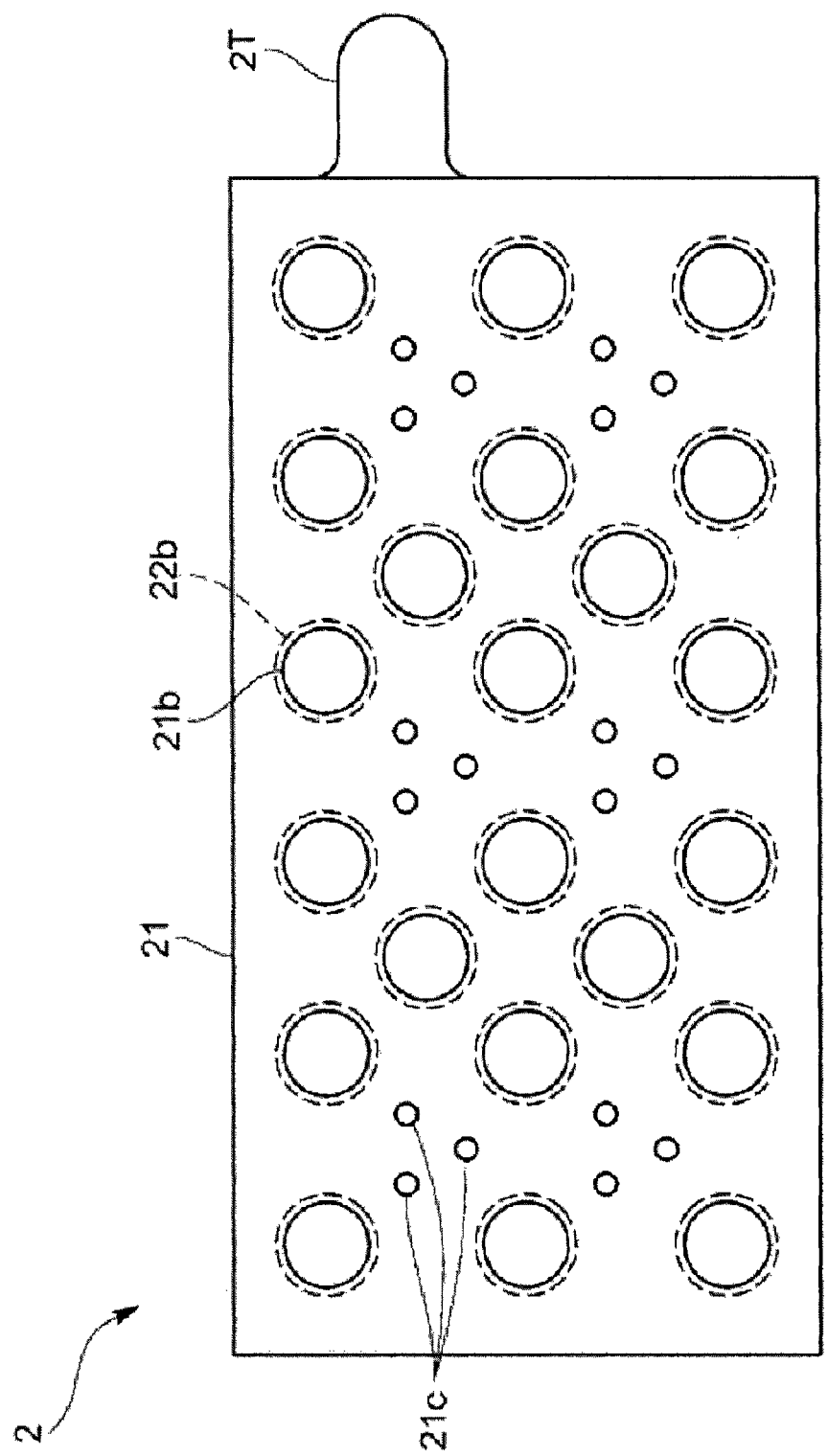
FIG. 3 is a plan view illustrating an electrode unit, according to example embodiments.

The plasma electrode unit 2, as shown in FIGS. 2 to 6B, includes a pair of electrodes 21 and 22 provided with dielectric films 21a and 22a on opposite surfaces thereof, and designated voltage is applied between the electrodes 21 and 22, thereby executing plasma discharge. The respective electrodes 21 and 22, particularly as shown in FIG. 3, have an approximately rectangular shape as seen from the top (the plane direction of the electrodes 21 and 22), and are formed of, for example, stainless steel, such as SUS403. Application terminals 2T to which voltage from the power supply 6 is applied are formed at the edges of the electrodes 21 and 22 of the electrode unit 2 (with reference to FIG. 3). Here, in a voltage application method of the plasma electrode unit 2 by the power supply 6, voltage in a pulse mode applied to the respective electrodes 21 and 22, a peak value of the voltage is within the range of 100V to 5,000V, and a pulse width of the voltage is within the range of 0.1 µs to 300 µs. Accordingly, an amount of generated ozone is suppressed, and thus, active species generated by plasma may be effectively discharged without loss due to a conventional filter, and sterilization of attached bacteria may be achieved for a short period of time.

Further, as shown in FIG. 5, the dielectric films 21a and 22a are formed on the opposite surfaces of the electrodes 21 and 22 by applying a dielectric, for example, barium titanate, to the opposite surfaces of the electrodes 21 and 22. Surface roughness (arithmetic average roughness Ra in this embodiment) of the dielectric films 21a and 22a is more than 0.1 µm and less than 100 µm. Otherwise, maximum height Ry and ten-point average roughness Rz may be used as the surface roughness. By restricting the surface roughness of the dielectric films 21a and 22a to a value within the above range, a gap is formed between the opposite surfaces of the electrodes 21 and 22 simply by stacking the electrodes 21 and 22, and plasma is formed within the gap. Accordingly, a spacer to form the gap to form plasma is not required between the respective electrodes 21 and 22. Further, control of the surface roughness of the dielectric films 21a and 22a by a thermal spray process is considered. As a non-limiting example, the dielectric applied to the electrodes 21 and 22 may use aluminum oxide, titanium oxide, magnesium oxide, strontium titanate, silicon oxide, silver phosphate, lead zirconate titanate, silicon carbide, indium oxide, cadmium oxide, bismuth oxide, zinc oxide, iron oxide, carbon nanotubes, or any combination thereof.

Further, as shown in FIGS. 3, 4, 6A and 6B, fluid passage holes 21b and 22b are provided at corresponding parts of the respective electrodes 21 and 22 so as to communicate with each other, and are configured, such that at least parts of the outlines of the fluid passage holes 21b and 22b are located at different positions as seen from the plane direction of the electrodes 21 and 22 (as seen from the top). That is, the shape of the fluid passage holes 21b formed on one electrode 21 as seen from the top and the shape of the fluid passage holes 22b formed on the other electrode 22 as seen from the top are different.

In more detail, the fluid passage holes 21b and 22b formed at the corresponding parts of the respective electrodes 21 and 22 have an approximately circular shape as seen from the top (with reference to FIGS. 3, 6A and 6B), and an opening size (an opening diameter) of the fluid passage holes 21b formed on the electrode 21 is smaller than an opening size (an opening diameter) of the fluid passage holes 22b formed on the electrode 22 by, for example, approximately 10 µm or more.

Figure 6A:
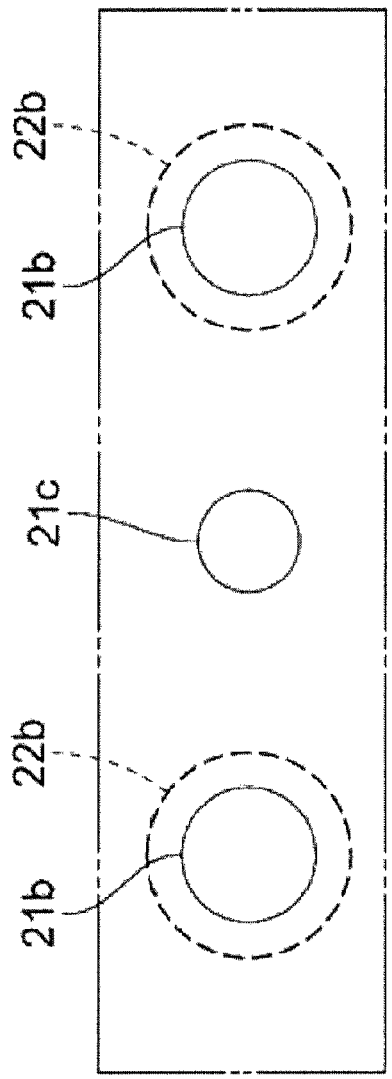
FIGS. 6A and 6B are a partially enlarged plan view and a sectional view schematically illustrating fluid passage holes and through holes, according to example embodiments.
Figure 6B:
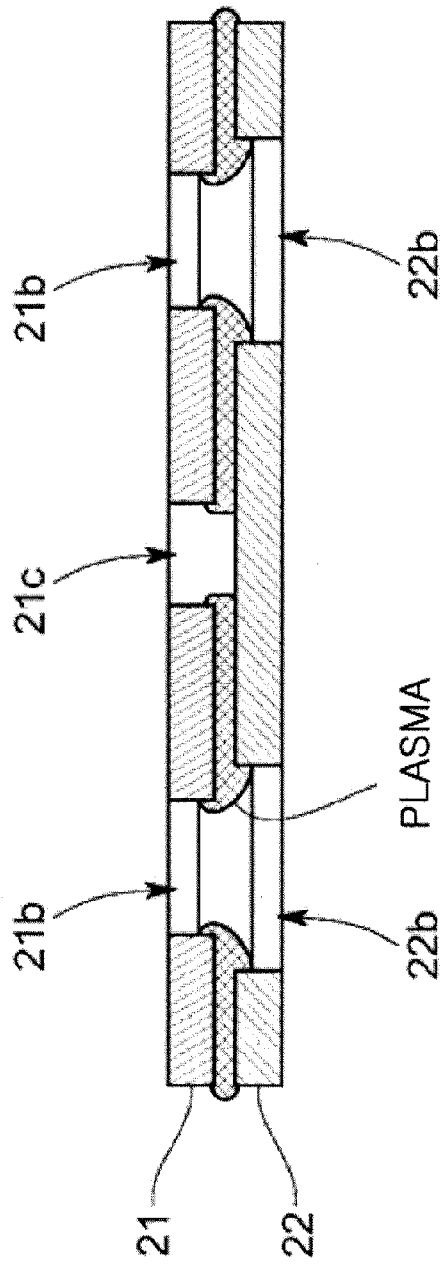

Further, as shown in FIGS. 3, 6A and 6B, the fluid passage holes 21b formed on the electrode 21 and the fluid passage holes 22b formed on the electrode 22 are concentric. Further, in this embodiment, all of the plural fluid passage holes 21b formed on the electrode 21 have the same shape, all of the plural fluid passage holes 22b formed on the electrode 22 have the same shape, and all of the fluid passage holes 21b formed on the electrode 21 are smaller than the fluid passage holes 22b formed on the electrode 22. Although this embodiment illustrates the fluid passage holes 21b and 22b as having an approximately circular shape, the fluid passage holes 21b and 22b are not limited to the circular shape, as long as at least parts of the outlines of the fluid passage holes 21b and 22b are located at different positions as seen from the top.

Further, as shown in FIGS. 3, 6A and 6B, the plasma electrode unit 2 is configured, such that through holes 21c are provided on one electrode 21 separately from the fluid passage holes 21b and 22b and openings of the through holes 21c on the opposite surface of the electrode 21 are closed by the other electrode 22. The fluid passage holes 21b and 22b formed on the respective electrodes 21 and 22 are referred to as complete opening parts, and for comparison with the complete opening parts, the through holes 21c are referred to as half opening parts.

An opening size of the through holes 21c is smaller than the opening size of the fluid passage holes 21b by approximately 10 µm or more. The through holes 21c are formed as substitutes for some of the regularly provided fluid passage holes 21b, and are provided around the fluid passage holes 21b (with reference to FIG. 3).

The air blowing device 3 is disposed adjacent to the other electrode 22 of the plasma electrode unit 2, and is provided with an air blowing fan which forcibly supplies air toward the fluid passage holes (complete opening parts) 21b and 22b formed on the plasma electrode unit 2. The air blowing device 3 generates an air current from the fluid passage holes 21b and 22b toward the absorption member 4. In more detail, a flow velocity of air blown by the air blowing device 3 and passing through the fluid passage holes 21b and 22b is in the range of approximately 0.1 m/s to 10 m/s.

Further, the air blowing device 3 functions to forcibly blow air toward a position opposite to the fluid passage holes 21b and 22b. In more detail, the air blowing device 3 may reverse an air blowing direction. The air blowing device 3 generates an air current from fluid passage holes 21b and 22b in the direction opposite to the absorption member 40. Accordingly, active species are discharged from the plasma electrode unit 2 to a space in front of the plasma electrode unit 2, thus being capable of sterilizing bacteria attached to an object located in front of the plasma electrode unit 2. In order to reverse the air blowing direction, in addition to reverse rotation of an air blowing fan serving as the air blowing device 3, a change unit to change the air blowing direction of the air blowing fan or a plurality of air blowing fans having different air blowing directions may be provided.

The absorption member 4 is disposed at the downstream of a fluid passing through the fluid passage holes 21*b* and 22*b* adjacent to one electrode 21 of the plasma electrode unit 2. In more detail, the absorption member 4 includes an absorbent formed of a porous material, such as silica gel, activated carbon, zeolite or mesoporous silica, or combinations thereof. The absorption member 4 has an approximately circular shape as seen from the top. Since odor materials (odor molecules), absorbed by the surface of the porous material become more stable in terms of energy than when they are independently present in air, absorption of these materials is spontaneously carried out without external electrical/mechanical force. Then, the absorption member 4 includes a plurality of through holes 4*h* formed in the air blowing direction. Accordingly, an air current generated from the air blowing device 3 easily contacts the absorption member 4 to effectively achieve deodorization and sterilization on the surface of the absorption member 4.

Figure 4:
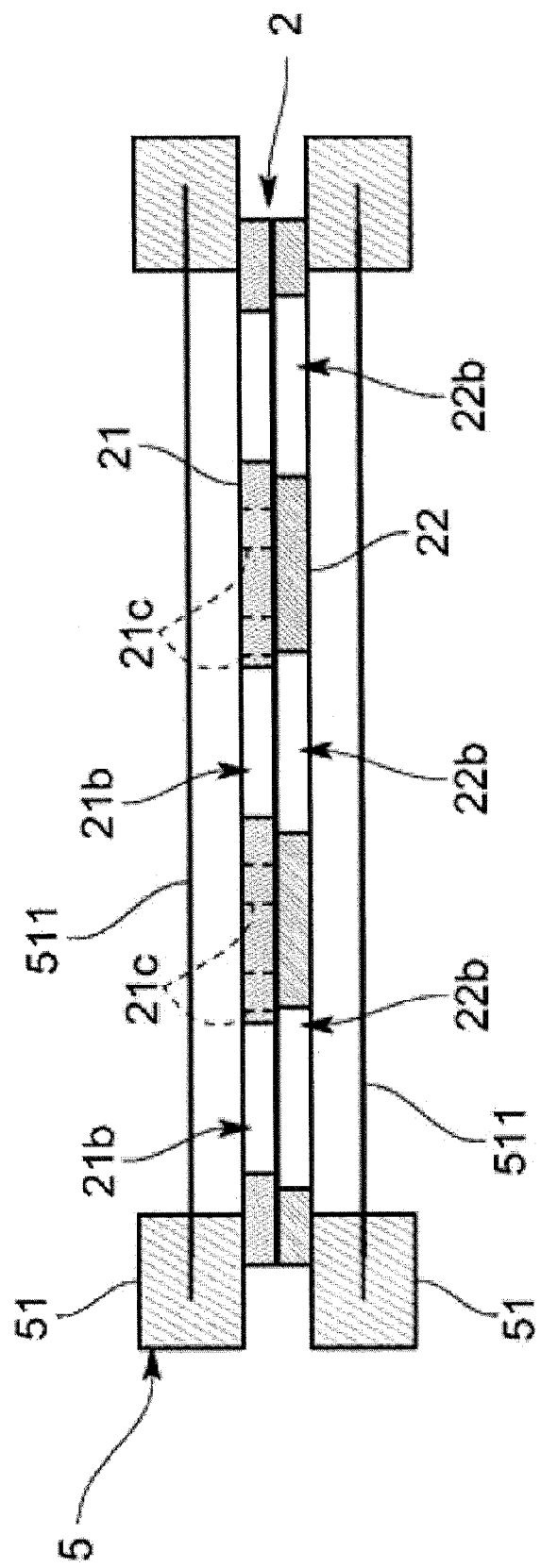
FIG. 4 is a cross-sectional view illustrating the electrode unit and an explosion proof device, according to example embodiments.

The explosion proof device 5 includes protective covers 51 disposed at the outside of the pair of the electrodes 21 and 22, as shown in FIG. 4, and prevents flames generated from a combustible gas, introduced into the fluid passage holes 21*b* and 22*b*, by plasma from propagating to the outside over the protective covers 51. In more detail, each of the protective covers 51 of the explosion proof device 5 includes a metal mesh 511 disposed at the outside of the pair of the electrodes 21 and 22, and the metal mesh 511 has a wire diameter of approximately 1.5 mm or less and an aperture ratio of approximately 30% or more.

Figure 7:
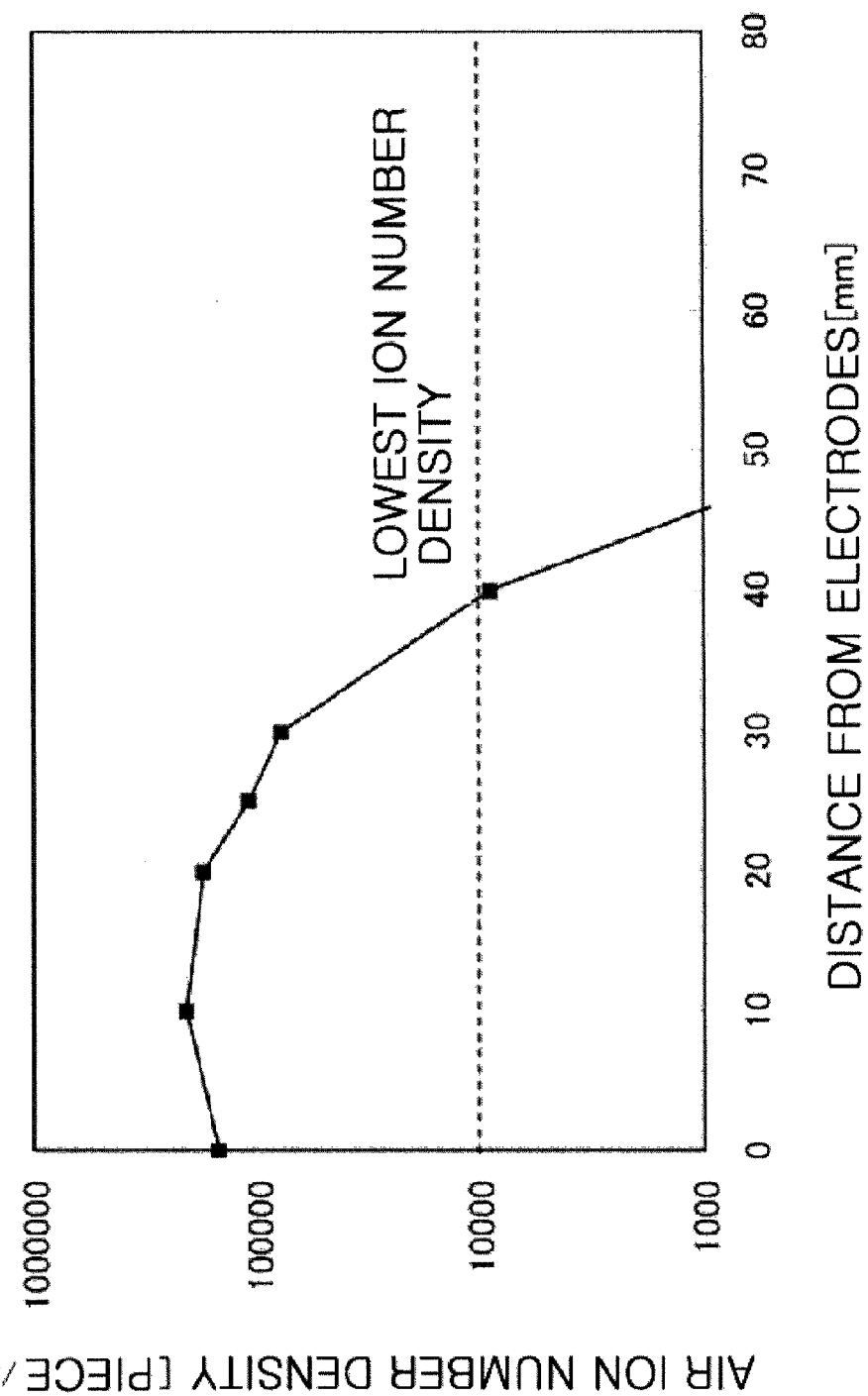
FIG. 7 is a graph illustrating measured distance dependency of ion number density, according to example embodiments.

Hereinafter, a test example using the deodorization and sterilization apparatus 100 in accordance with this embodiment will be described. First, distance dependency of ion number density will be described. FIG. 7 is a graph illustrating distance dependency of negative ion number density measured by an air ion measurement instrument. From among active species generated by plasma, most of ions detected as air ions are ions having relatively long life and low activity, and in this test example, air ion concentration is used as an index using relations between an amount of generated active species and detected ions. As shown in FIG. 7, the concentration of ions generated by the electrode unit 2 is highest at a position separated from the electrodes by a distance of several cm and tends to decrease as the distance from the electrodes increases. The distance at which the highest concentration of ions is detected depends on an air velocity or other environmental factors, but installation of the surface of the absorption member 4, within the distance at which the highest concentration of ions is detected, is important. In more detail, the surface of the absorption member 4 needs to be installed at a position of more than the lowest ion number density ($10,000/cm^3$) required for a sterilizing capacity, which will be described later.

Figure 8:
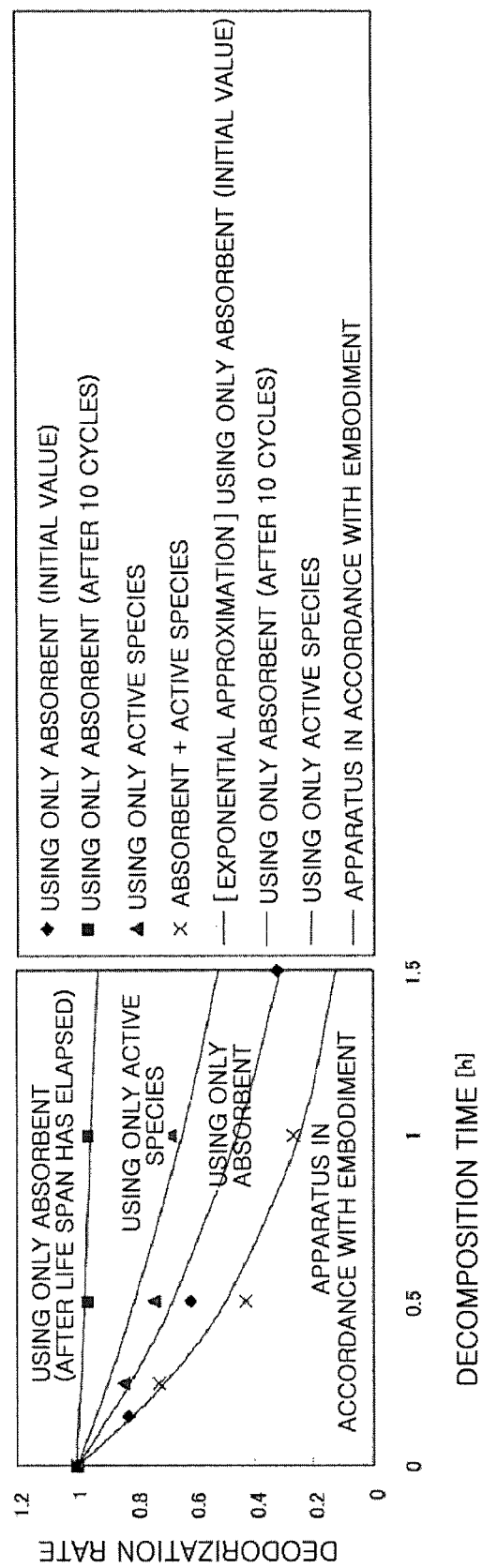
FIG. 8 is a graph illustrating variation of decomposition of odor concentration in accordance with respective deodorization methods, according to example embodiments.
Figure 9:
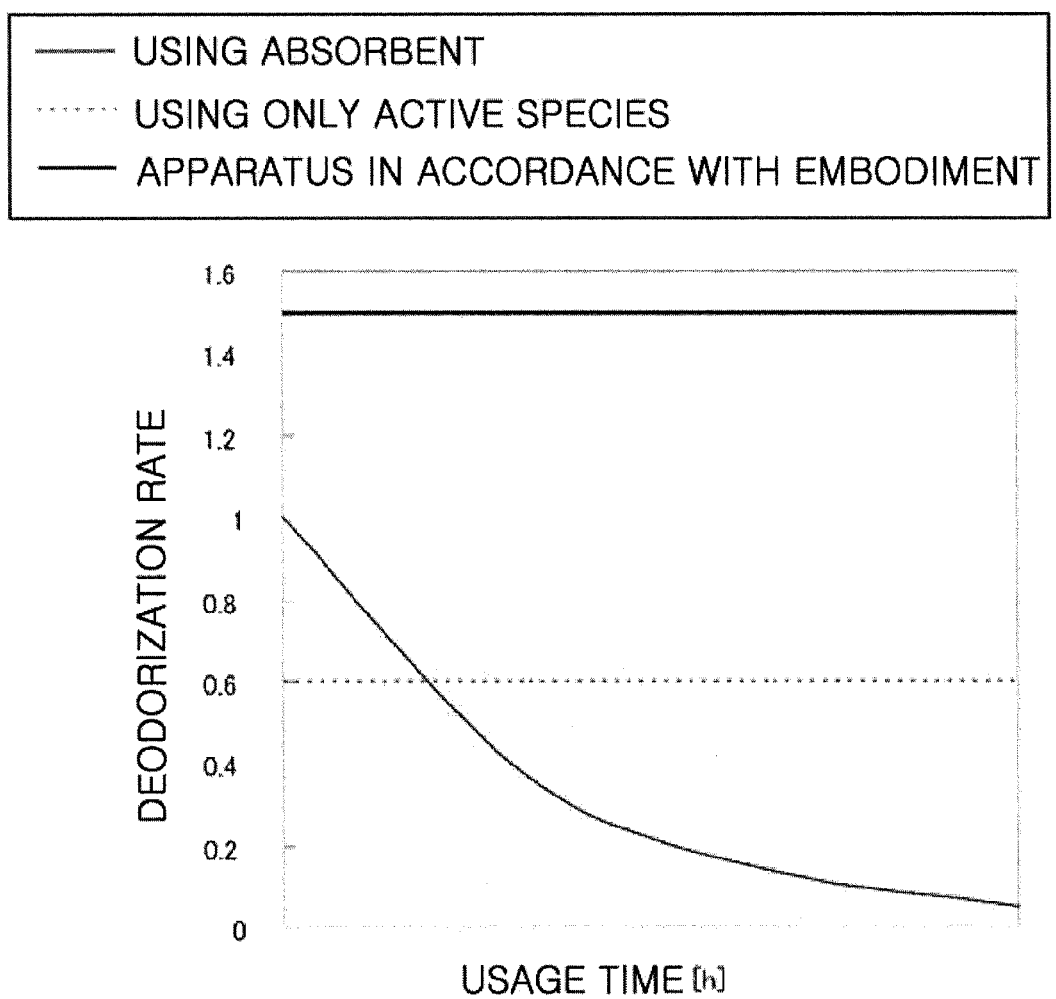
FIG. 9 is a graph illustrating variation of time of deodorization efficiency in accordance with respective deodorization methods, according to example embodiments.

Next, deodorization on the surface of the absorption member 4 will be described. As shown in FIG. 8, as a result of deodorization due to absorption, an odor concentration curvilinearly decreases. However, as absorption is repeated, time taken to achieve deodorization gradually increases because usable absorption sites are gradually reduced, and finally, absorption is not executed, and thus, deodorizing effects are no longer exhibited. That is, the absorption member (absorbent) 4 has a life. Since the concentration of the active species generated by plasma in deodorization due to active species does not depend on elapsed time, deodorization due to active species does not have a life differing from deodorization due to absorption. Therefore, deodorization using a combination of characteristics of the two deodorization methods, i.e., deodorization due to absorption and deodorization due to active species, reduces time taken to achieve deodorization and does not lower a deodorizing capacity even if the absorption member and the active species are repeatedly exposed to odors. The reason for this is that saturation absorption, which is a drawback of deodorization due to absorption continuously exhibits absorption performance through decomposition due to the active species. Therefore, if odor concentration is continuously changed and a source generating odors is present as in an actual usage environment, deodorization efficiency of a case using only the absorbent is gradually lowered, as compared with the deodorization and sterilization apparatus 100 in accordance with the embodiment exhibiting uniform deodorization efficiency, as shown in FIG. 9.

Figure 10:
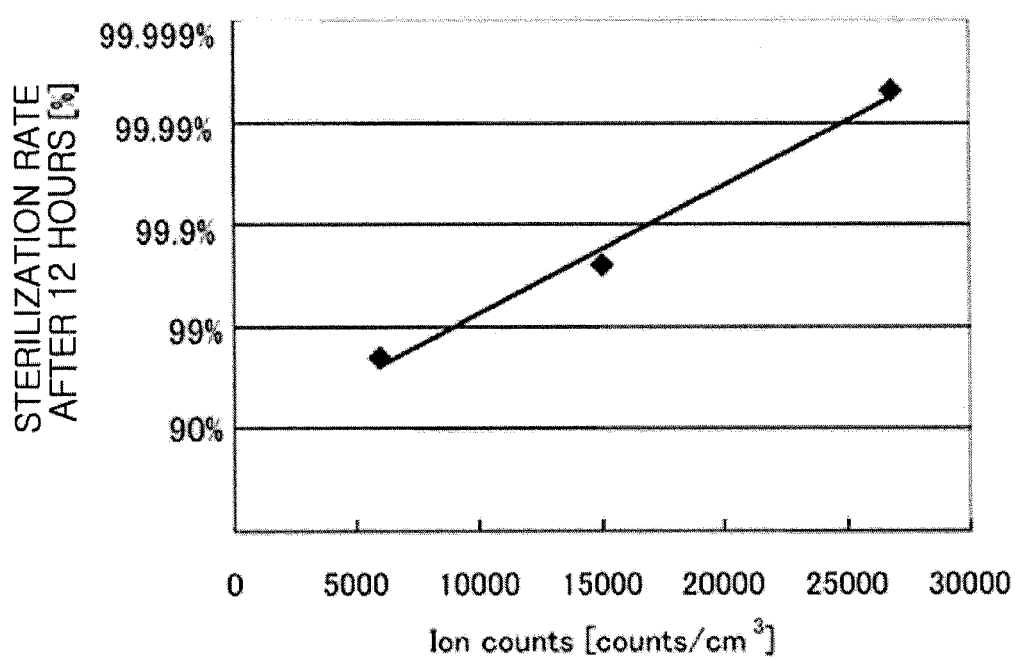
FIG. 10 is a graph illustrating dependency of sterilization rates to attached bacteria on ion number density, according to example embodiments.

Thereafter, sterilization of attached bacteria executed by changing an air blowing direction will be described. In a demonstration test, an object to be sterilized is colon bacilli, active species are discharged to a medium to which colon bacilli are applied in a chamber having a volume of 100 L for 6 hours, colon bacilli are cultured, and then the number of formed colonies is counted. FIG. 10 illustrates sterilization rates calculated after 12 hours, as a result of the test. It is understood from FIG. 10 that the sterilization rate depends on an amount of generated active species and nearly complete sterilization, e.g., a sterilization rate of 99%, is achieved in a condition of an air ion number density of about $10,000/cm^3$ or more.

Figure 11:
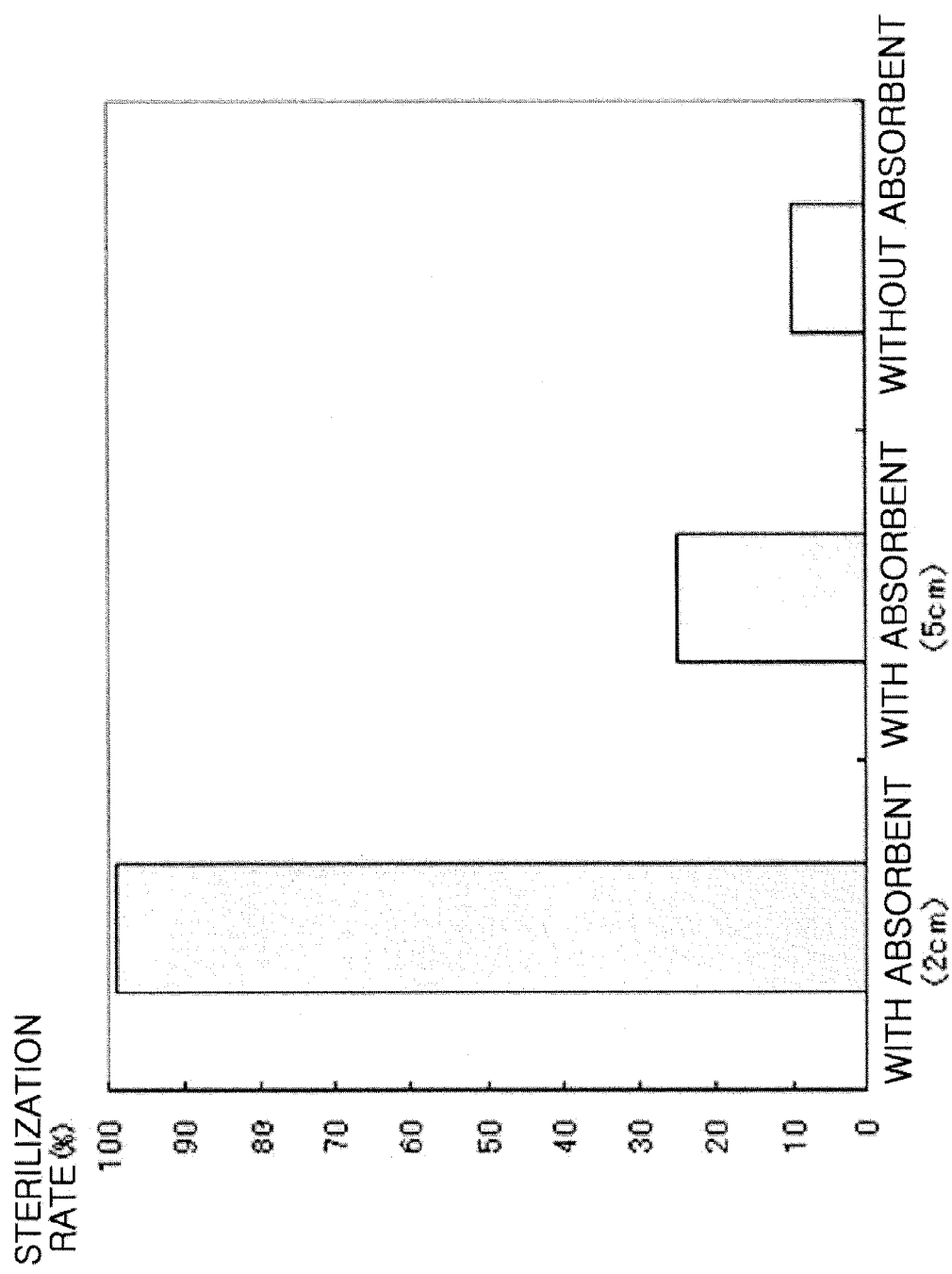
FIG. 11 is a graph illustrating differences of sterilization rates between presence and absence of an absorbent, according to example embodiments.

Thereafter, sterilization of floating bacteria executed on the surface of the absorption member 4 will be described. FIG. 11 is a graph illustrating differences of sterilization rates among a case in which the absorbent member 4 is disposed at a position separated from the electrode unit 2 by a distance of 2 cm (within the range of the above-described lowest ion number density), a case in which the absorbent member 4 is disposed at a position separated from the electrode unit 2 by a distance of 5 cm (at the outside of the range of the above-described lowest ion number density), and a case in which the absorbent member 4 is not used. In a demonstration test, an object to be sterilized is colon bacilli, active species are discharged under the condition that the absorption member 4 is disposed at the downstream of an air current from the electrodes, and then, the number of live bacteria on the surface of the absorption member 4 is measured. In the case that the absorbent member 4 is disposed at the position separated from the electrode unit 2 by the distance of 2 cm, a sterilization rate of 99% is achieved after 6 hours, and in the case that the absorbent member 4 is disposed at the position separated from the electrode unit 2 by the distance of 5 cm, a sterilization rate is remarkably reduced to 25%. Further, in the case that the absorbent member 4 is not disposed, a sterilization rate is further reduced to 10%. Accordingly, it is understood that the sterilization rate is remarkably improved by disposing the absorption member 4, and further, a sterilizing capacity depends on the amount of generated active species (the distance of the absorption member from the electrodes).

Figure 12:
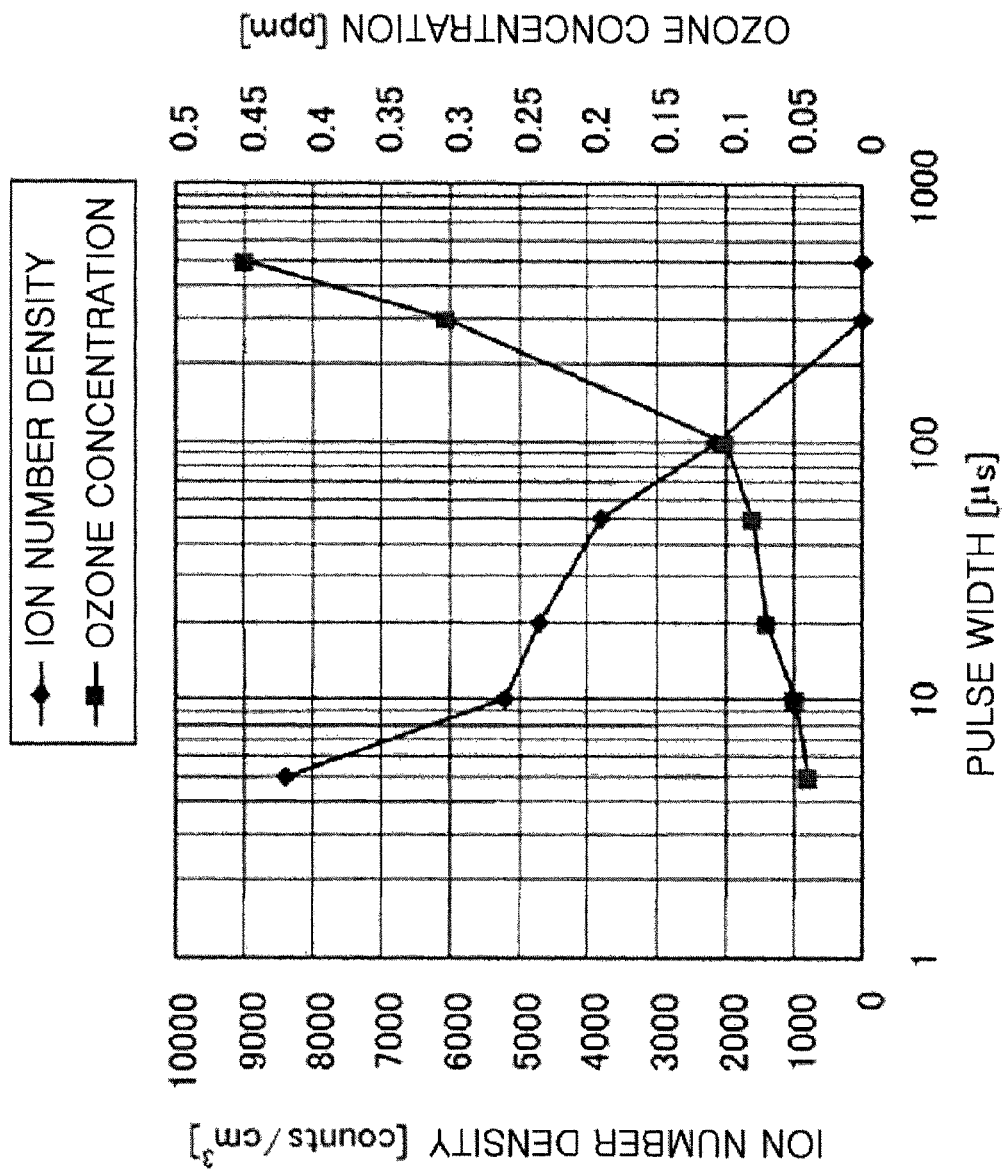
FIG. 12 is a graph illustrating pulse width dependency of ion number density and ozone concentration, according to example embodiments.

Thereafter, an ozone generation suppressing method required to achieve sterilization of attached bacteria and floating bacteria will be described. FIG. 12 is a graph illustrating pulse width dependency of ion number density and ozone concentration. In this case, pulse width dependency of ion number density and ozone concentration is measured when only a pulse width is changed, while allowing a repetition frequency and a peak voltage value of a pulse to be uniformly maintained at approximately 1 k. As shown in FIG. 12, the ion number is measured and an ozone concentration is lowered at a pulse width of approximately 100 μs or less, and as a pulse width is decreased, the ion number is increased and the ozone concentration is decreased. Consequently, the ozone concentration may be suppressed by lowering the pulse to approximately 100 μs or less.

Figure 13:
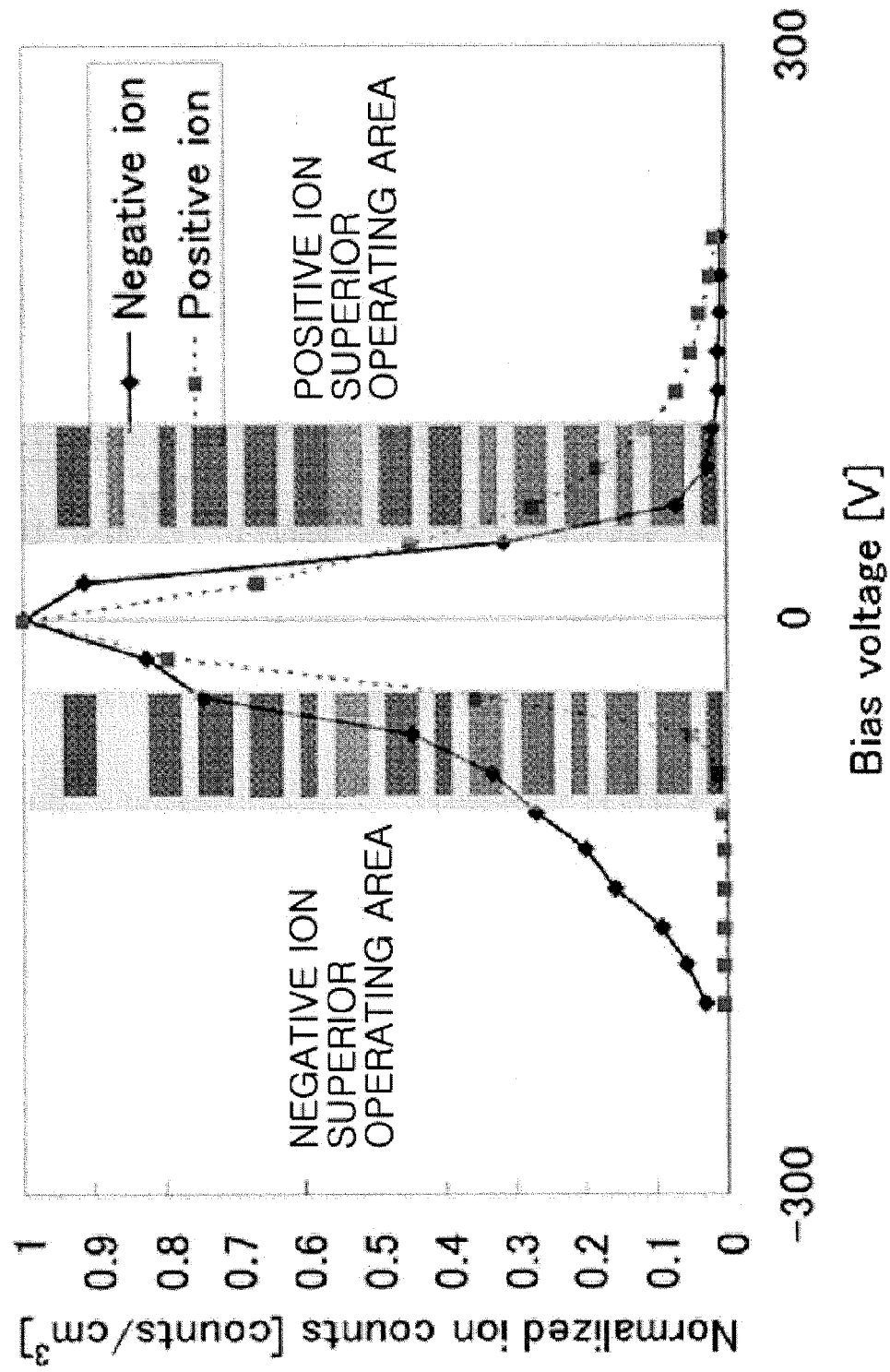
FIG. 13 is a graph illustrating ion polarity and amounts of generated ions according to bias voltage, according to example embodiments.

Thereafter, a method of controlling balance between polarity of generated ions and an amount of the generated ions by applying bias of a DC component to applied voltage. It is expected that kinds of active species optimal to decompose odor materials or absorbed to the absorption member 4 or floating bacteria are different. Therefore, increase of generation of active species most greatly contributing to deodorization or sterilization, by controlling the polarity or amount of ions, is effective in increasing the deodorization efficiency and sterilization rate. As shown in FIG. 13, by changing DC bias voltage, a ratio of generated ions may be controlled from among a condition in which a large amount of positive ions is generated, a condition in which a large amount of negative ions is generated, and a condition in which both positive ions and negative ions are generated.

In the above-described deodorization and sterilization apparatus 100 in accordance with this embodiment, a contact area between plasma generated from the respective corresponding fluid passage holes 21b and 22b and a fluid is increased, thereby increasing an amount of generated active species. Further, since the absorption member 4 is disposed at the downstream of the fluid passage holes 21b and 22b, even if air having passed through the fluid passage holes 21b and 22b includes floating bacteria, which are not non-activated or odor materials which are not decomposed, the floating bacteria and the odor materials may be collected at one place through absorption via the absorption member 4 and high-efficiency sterilization and deodorization of the floating bacteria and the odor materials may be achieved by contact of the active species with the absorption member 4.

The disclosure is not limited to the above embodiment of the present disclosure.

For example, although the above embodiment illustrates one absorption member as corresponding to one plasma electrode unit, a plurality of absorption members corresponding to one electrode may be disposed, or a plurality of plasma electrode units corresponding to one absorption member may be disposed.

Figure 14:
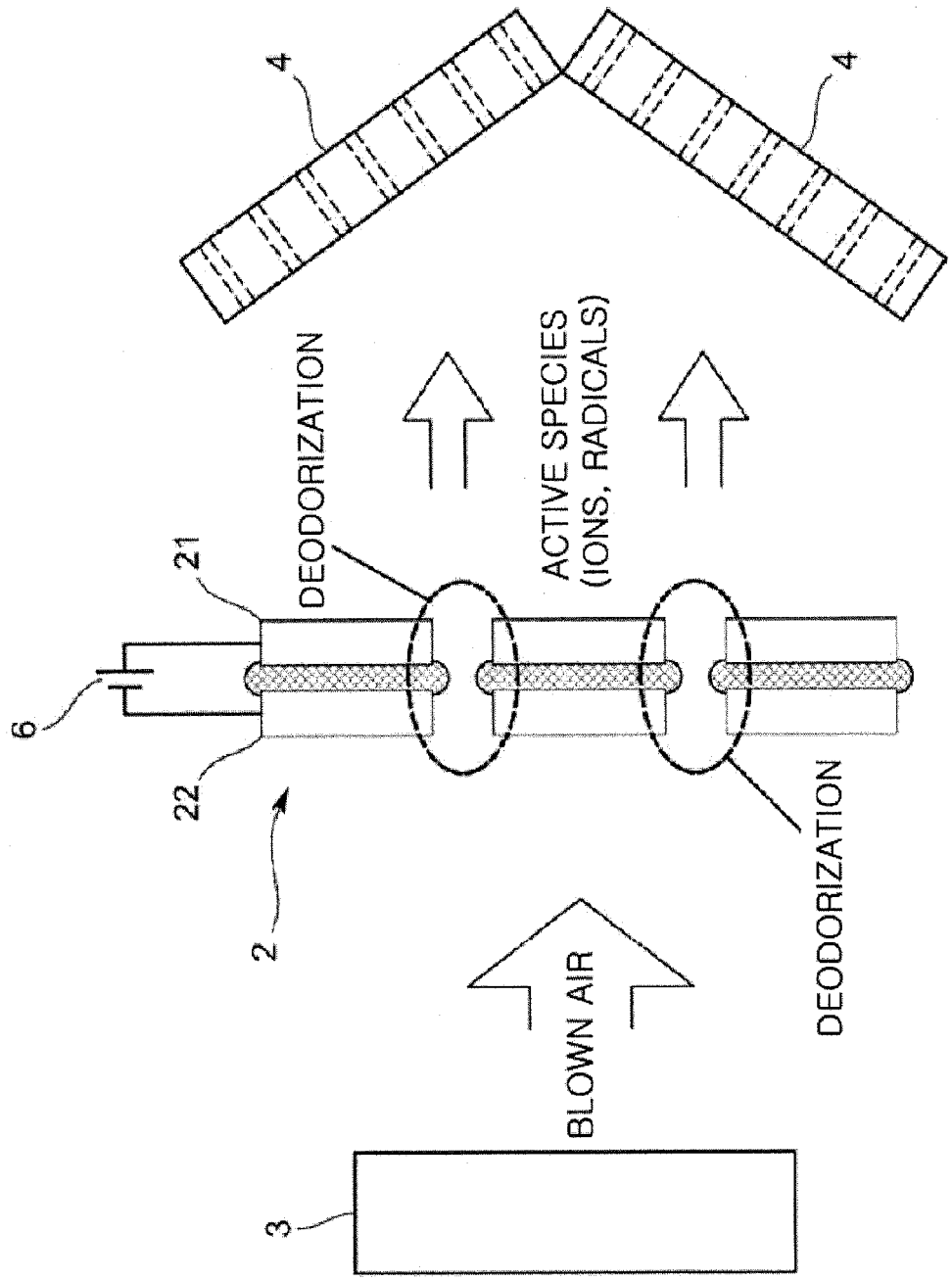
FIG. 14 is a view illustrating one example of disposition of absorption members, according to example embodiments.
Figure 15:
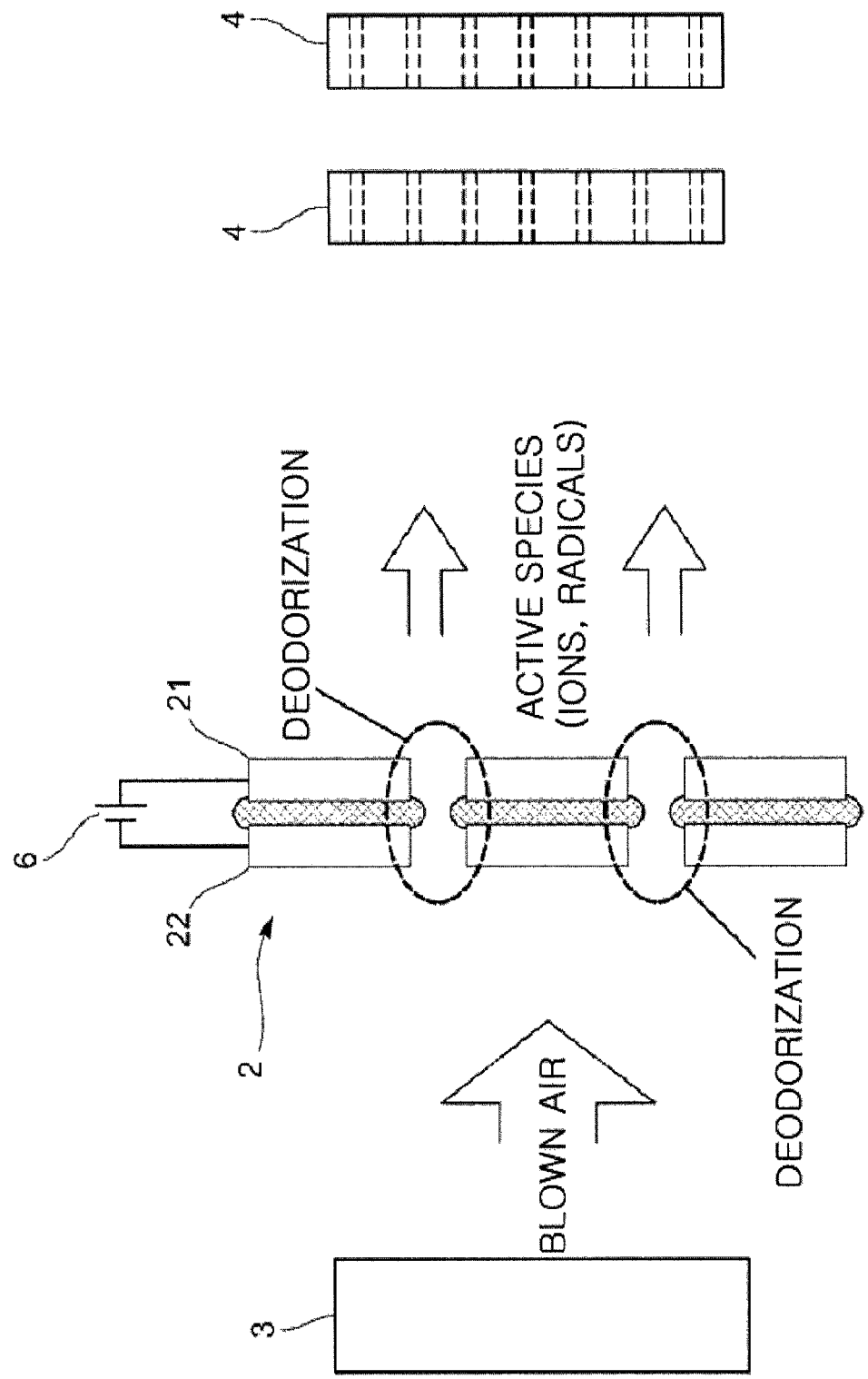
FIG. 15 is a view illustrating another example of disposition of the absorption members, according to example embodiments.

If a plurality of absorption members is disposed, disposition of absorption members 4 having different absorbing capacities may be considered, as shown in FIGS. 14 and 15. As an example of disposition of the absorption members 4, the plural absorption members 4 may be disposed in parallel, as shown in FIG. 14, or be disposed in series, as shown in FIG. 15. If the plural absorption members 4 are disposed in series, the absorption member 4 having an absorbing capacity optimized for absorption of large diameter particles and the absorption member having an absorbing capacity optimized for absorption of small diameter particles may be sequentially disposed from the plasma electrode unit 2.

Further, in order to allow through holes of the absorption members to effectively pass air, a rectifying plate may be provided at the upstream of the absorption members.

Figure 16:
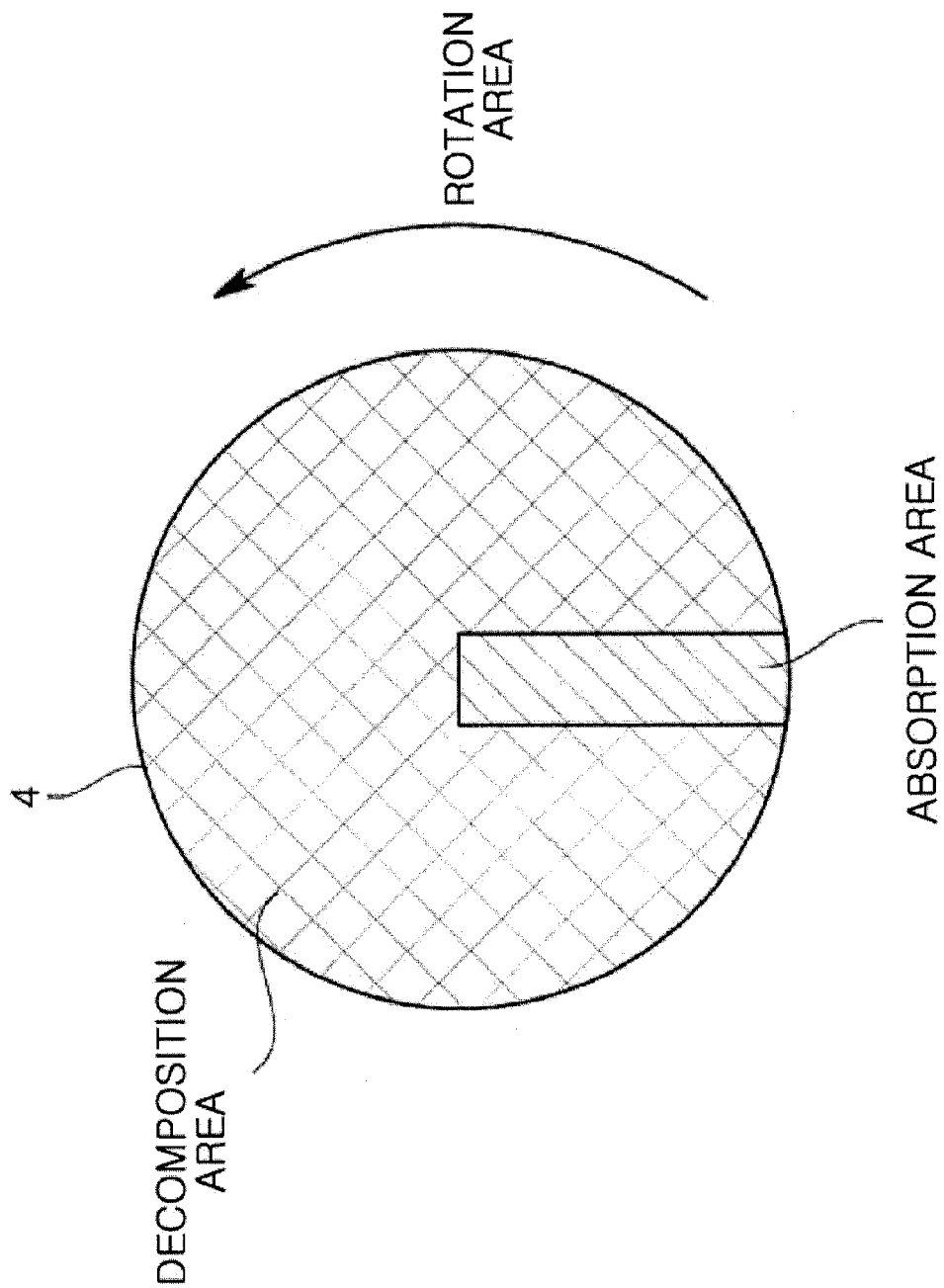
FIG. 16 is a view illustrating an absorption area and a decomposition area if a circular absorption member is rotated, according to example embodiments.

Further, although this embodiment illustrates the absorption member as being formed by applying an absorbent to a flat plate, a circular absorption member 4 may be provided to be rotated, as shown in FIG. 16. In more detail, while the absorption member 4 is rotated once, floating bacteria and odor materials absorbed to the absorption member 4 moves between an absorption area which air containing floating bacteria and odor materials contacts, and a decomposition area in which sterilization and deodorization due to active species generated from the electrodes is executed, thus being sterilized. Further, instead of the rotary circular absorption member 4, a sheet-type absorption member may be circulated by a circulation device so that an absorption area and a decomposition area are alternated.

The absorption member may have various shapes, such as a rectangular shape and a polygonal shape, as seen from the top, in addition to a circular shape, as described in the above embodiment.

Further, the absorption member may be formed by retaining an absorbent on a mesh-type base, in addition to application of the absorbent to the flat plate. In this case, the absorbent may be retained on the metal meshes of the explosion proof device to form the absorption member, thereby simplifying the configuration of the apparatus.

Further, an ultraviolet lamp may be disposed adjacent to the absorption member and be used as a subsidiary unit for sterilization and deodorization, or the surface of the absorption member may be impregnated with a photocatalyst and an ultraviolet lamp may irradiate ultraviolet rays thereto.

Figure 17:
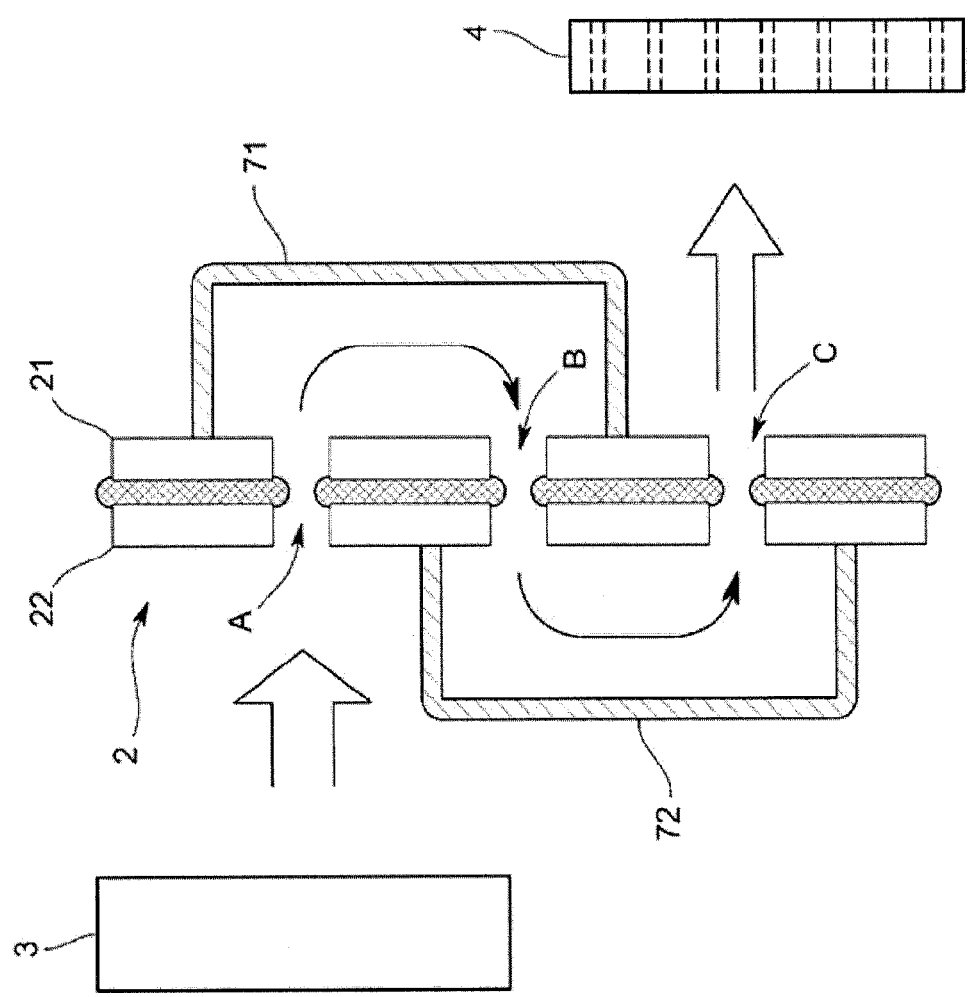
FIG. 17 is a view illustrating a deodorization and sterilization apparatus having a path formation member, according to example embodiments.

Further, a path formation member 7 forming a path, through which plural fluid passage holes A~C communicate with each other such that the fluid passage hole A at one end of the path formed by the path formation member 7 faces the upstream in the air blowing direction and the fluid passage hole C at the other end of the path formed by the path formation member 7 faces the absorption member 4, may be provided, as shown in FIG. 17. In more detail, the path formation member 7 includes at least a first path formation part 71 installed at one electrode 21 of the plasma electrode unit 2 and a second path formation part 72 installed at the other electrode 22. With reference to FIG. 17, the first path formation part 71 communicates the fluid passage holes A with the fluid passage hole B adjacent to the fluid passage hole A. Further, the second path formation part 72 communicates the fluid passage holes B with the fluid passage hole C. An opening at the upstream of the fluid passage hole A and an opening at the downstream of the fluid passage hole C communicate with each other by the path formation member 71 and 72.

Figure 18:
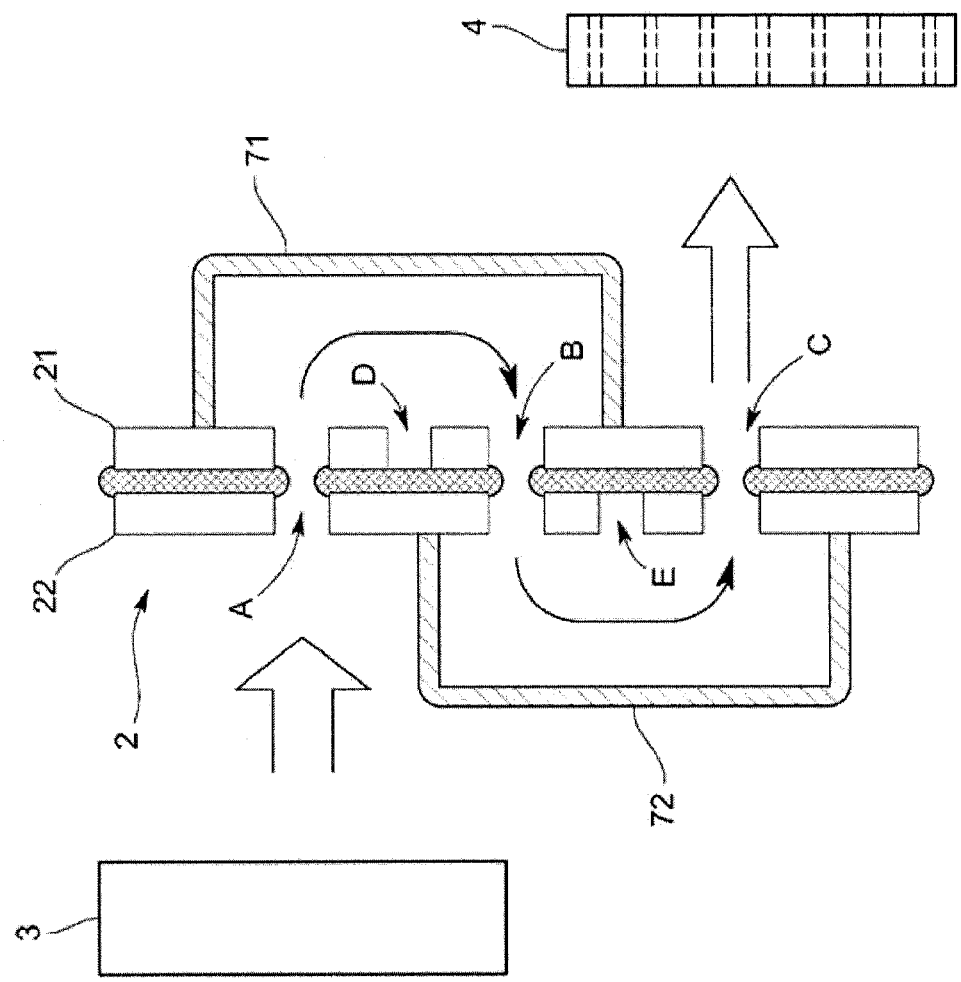
FIG. 18 is a view illustrating another deodorization and sterilization apparatus having a path formation member, according to example embodiments.

In this case, as shown in FIG. 18, the first path formation part 71 may communicate a through hole D formed on the electrode 21 with the fluid passage holes A and B as well as communicate the fluid passage hole A and the fluid passage hole B with each other, and the second path formation part 72 may communicate a through hole E formed on the electrode 22 with the fluid passage holes B and C as well as communicate the fluid passage hole B and the fluid passage hole C with each other. Thereby, a deodorizing capacity may be further improved.

If the above-described path formation member 71 and 72 is prepared, an absorbent may be provided on the inner surface of the path formation member 71 and 72 to absorb floating bacteria and odor materials in air. Thereby, the deodorizing capacity may be further improved.

Figure 19:
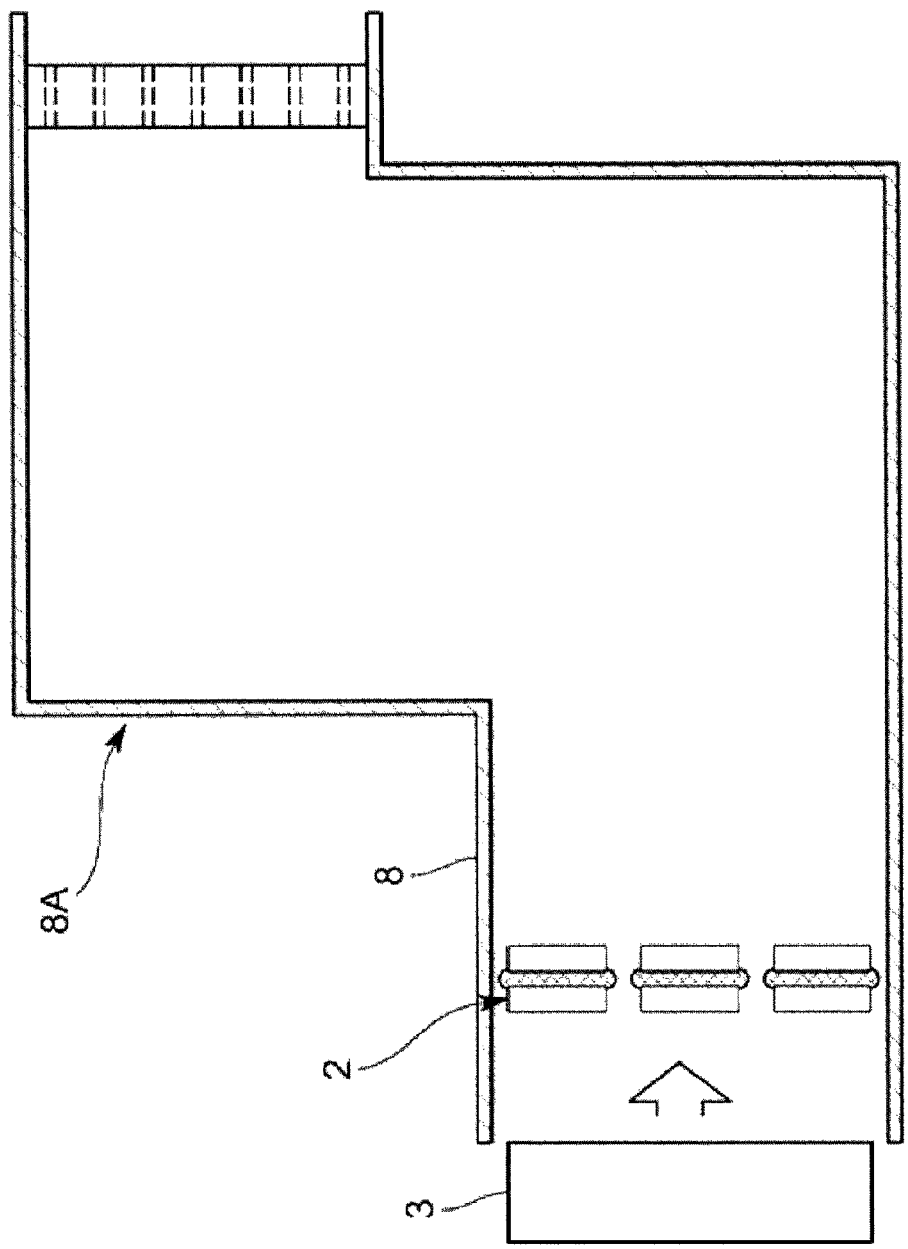
FIG. 19 is a view illustrating a deodorization and sterilization apparatus having an introduction path formation member, according to example embodiments.

Further, an introduction path formation member 8 to guide active species generated via the fluid passage holes 21 and 21b to the absorption member 4 may be provided between the plasma electrode unit 2 (the fluid passage holes 21 and 22b) and the absorption member 4. The introduction path formation member 8 has a retaining structure 8A to retain the active species. As the retaining structure 8A, a part of the introduction path formation member 8 may be enlarged to have an increased cross-sectional area of a path to retain an air current, as shown in FIG. 19. Thereby, the introduction path formation member 8 having the retaining structure 8A elongates reaction time, as compared with a rectilinear path without a retaining part, thus increasing sterilization and deodorization efficiency.

In addition, an eddy-shaped or maze-shaped introduction path may be provided to enlarge contact time between active species and odor materials/floating bacteria, thereby increasing sterilization and deodorization efficiency.

If the above-described introduction path formation member is prepared, an absorbent may be provided on the inner surface of the introduction path formation member to absorb floating bacteria and odor materials in air. Accordingly, the deodorizing capacity may be further improved.

Figure 20:
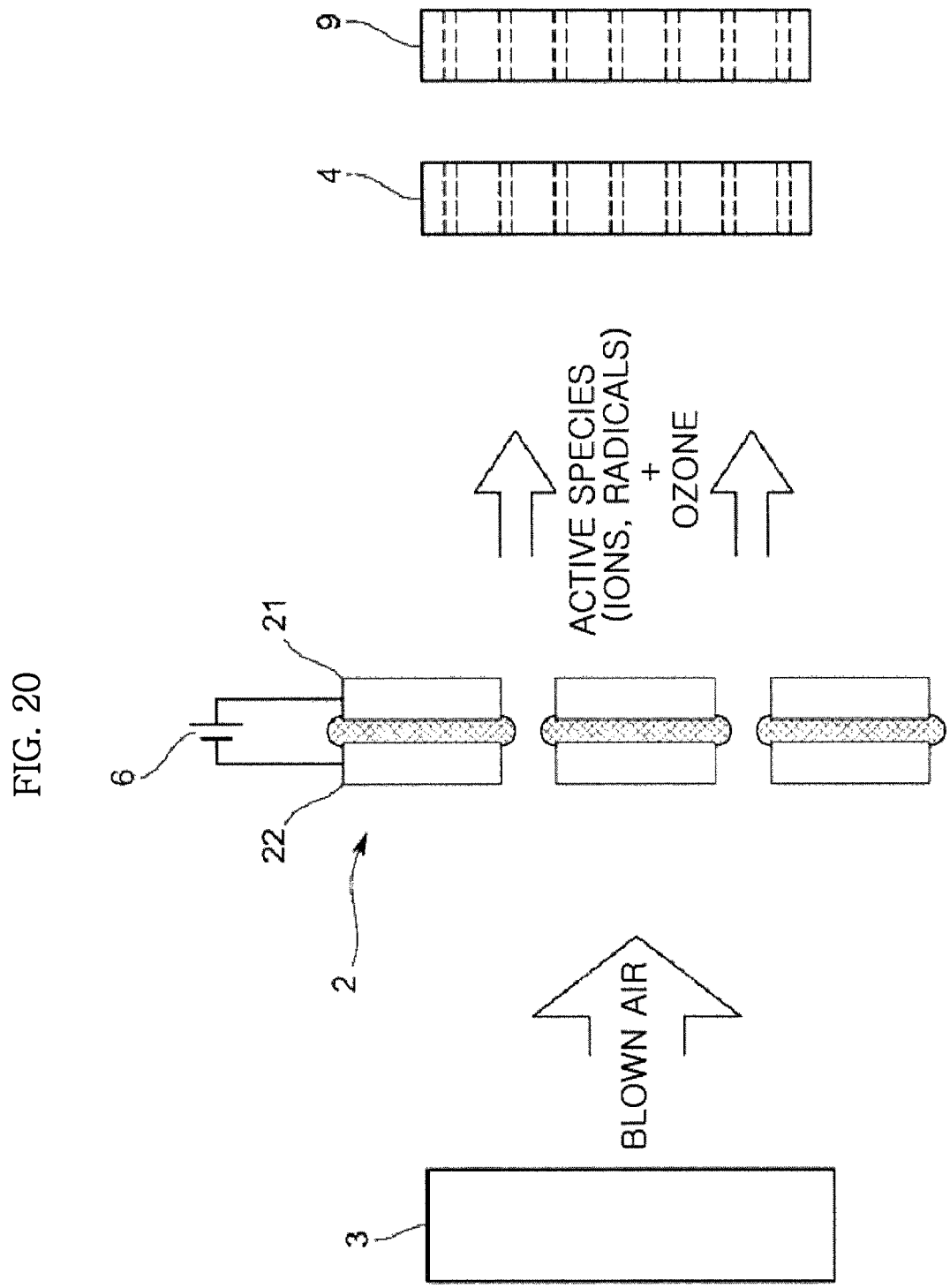
FIG. 20 is a view illustrating a deodorization and sterilization apparatus having an ozone decomposition catalyst, according to example embodiments.

Further, although this embodiment illustrates that generation of ozone is reduced by applying pulse voltage, ozone may be actively utilized. In this case, as shown in FIG. 20, an ozone decomposition catalyst 9 is disposed adjacent to the absorption member 4 at the downstream of the plasma electrode unit 2. Accordingly, deodorization and sterilization effects due to ozone may be obtained, and thus, the apparatus may exhibit more effective deodorization and sterilization effects.

Figure 21:
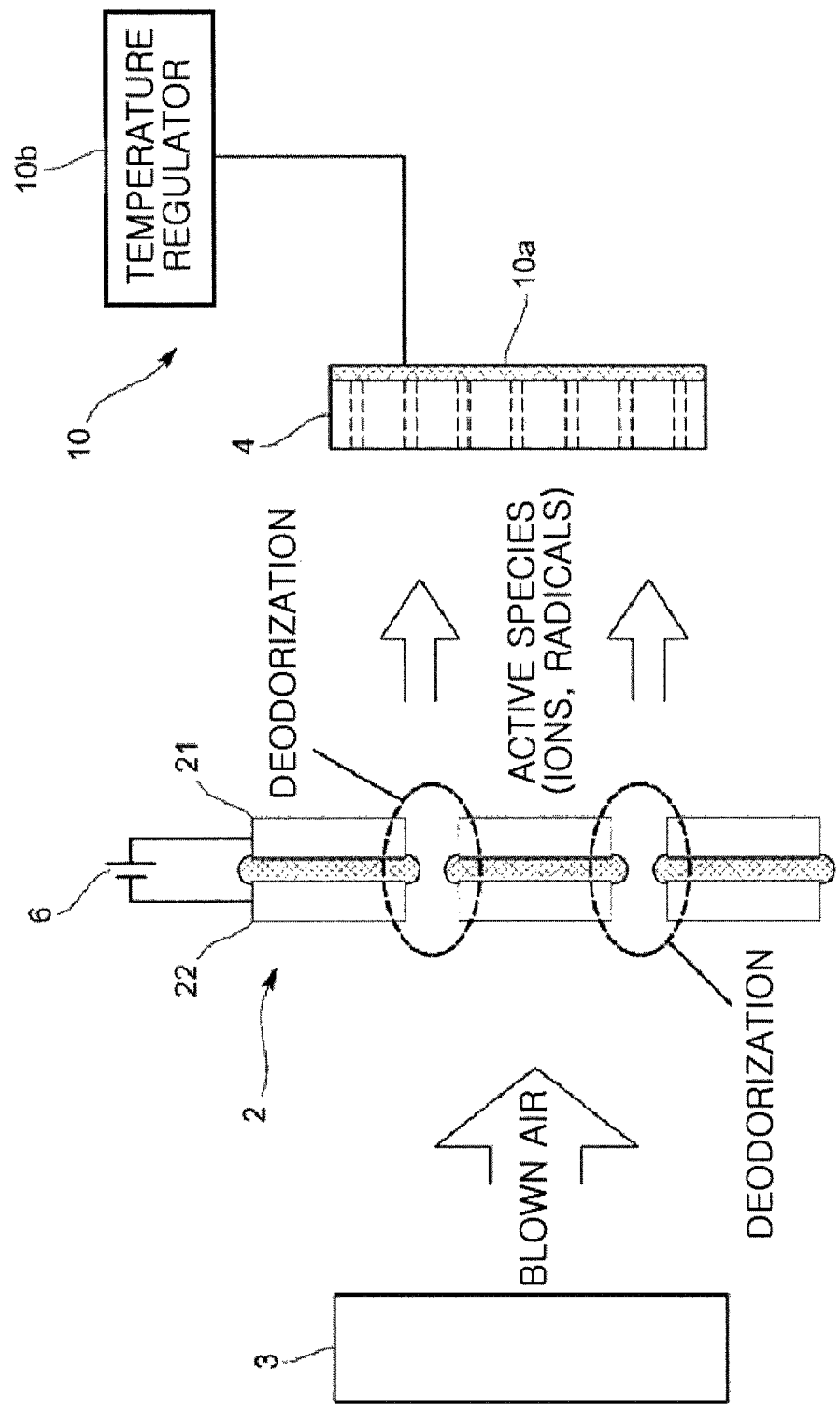
FIG. 21 is a view illustrating a deodorization and sterilization apparatus having a refresh function, according to example embodiments.

Further, the deodorization and sterilization apparatus in accordance with this embodiment may have a refresh function. Such a refresh function may be obtained by a heating device 10 to heat the absorption member 4, as shown in FIG. 21. The heating device 10 includes, for example, a heater 10a to heat the absorption member 4 and a temperature regulator 10b to control the heater 10a. The heating device 10 periodically heats the absorption member 4, thereby re-discharging odor materials accumulated on the surface of the absorption member 4. At this time, the plasma electrode unit 2 supplies active species using the air blowing device 3, thereby achieving deodorization and sterilization of the re-discharged odor materials and floating bacteria. Accordingly, the absorbing capacity of the absorption member 4 may be recovered.

Figure 22:
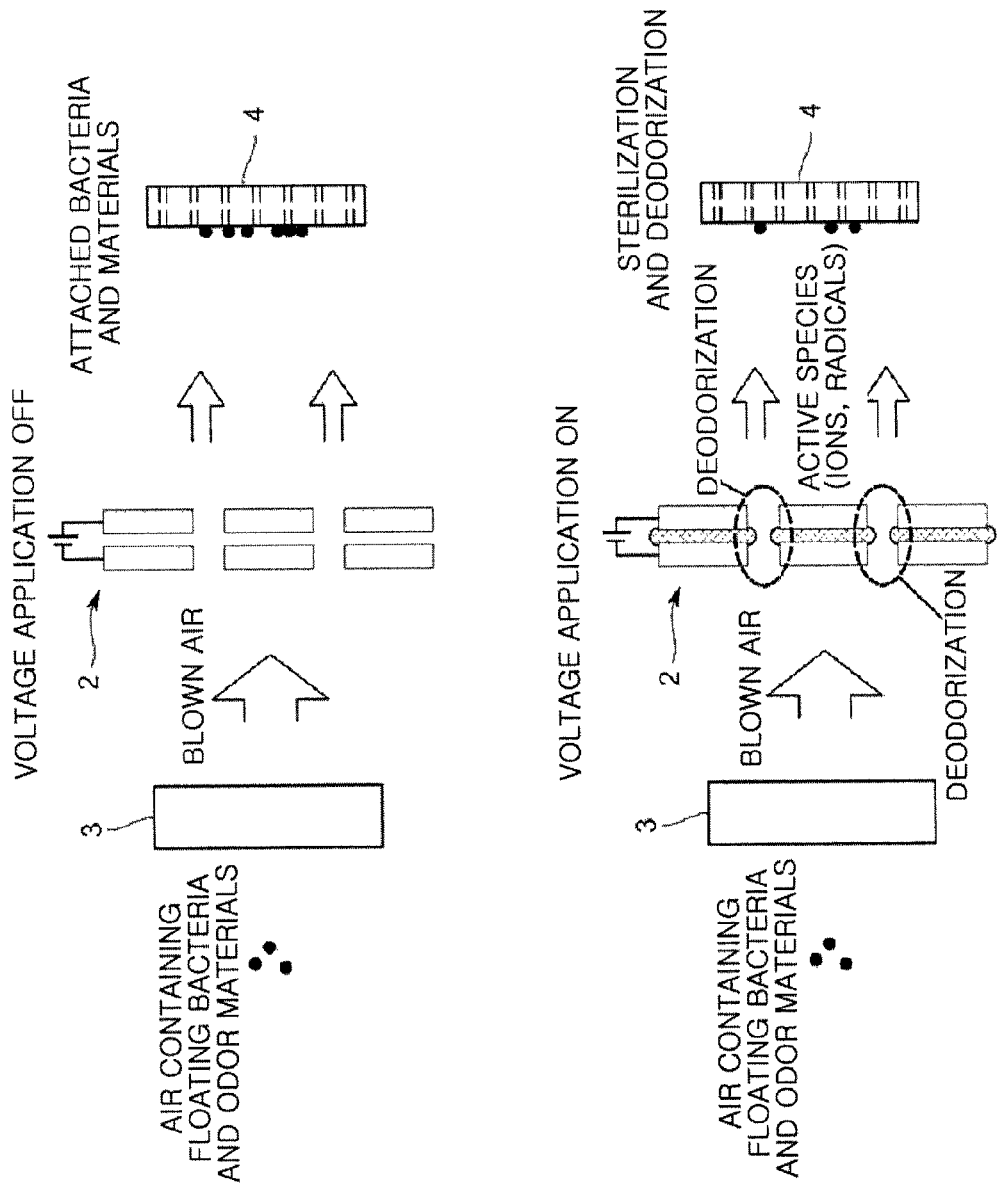
FIG. 22 is a view illustrating an operating method of the deodorization and sterilization apparatus, according to example embodiments.

Further, the deodorization and sterilization apparatus 100 in accordance with this embodiment may be configured to individually exhibit an absorption function and a decomposition function. In more detail, for example, as shown in FIG. 22, an absorption mode in which application of voltage to the plasma electrode unit 2 is stopped and air blown by the air blowing device 3 is executed simultaneously to allow the absorption member 4 to absorb floating bacteria or odor materials, and a decomposition mode in which voltage is applied to the plasma electrode unit 2 after the absorption mode to supply active species generated by plasma to the absorption member 4, may be provided to be switched. Here, a sensor (not shown) may be provided at the downstream of the absorption member 4 so as to detect the absorbing capacity of the absorption member 4 and to execute mode switching between the absorption mode and the decomposition mode using a result of the detection. Further, feedback control of an amount of air blown by the air blowing device 3 may be carried out using the result of the detection.

Although this embodiment illustrates the deodorization and sterilization apparatus as having the air blowing device, the air blowing device may be omitted if the deodorization and sterilization apparatus is used at a place where an air current is generated (for example, the inside of a tub of a washing machine, an air blowing unit of an electric fan, etc.). In this case, the plasma electrode unit may be disposed at the upstream of the air current and the absorption member may be disposed at the downstream of the air current.

Although this embodiment illustrates the absorption member and the air blowing device as being separately disposed, the absorbent may be provided on the entirety or a portion of the air blowing device so that the air blowing device itself has an absorbing capacity.

Although this embodiment illustrates the plural fluid passage holes 21b of the electrode 21 as having the same shape and the plural fluid passage holes 22b of the electrode 22 as having the same shape, the plural fluid passage holes 21b and the plural fluid passage holes 22b may have different shapes.

Further, although this embodiment illustrates all of the fluid passage holes 21b of the electrode 21 as being larger or smaller than all of the fluid passage holes 22b of the electrode 22, some of the fluid passage holes 21b of the electrode 21 may be smaller than the fluid passage holes 22b of the electrode 22, and the remaining fluid passage holes 21b may be larger than the fluid passage holes 22b of the electrode 22.

Moreover, although this embodiment illustrates the through holes as being formed on either of the electrodes 21 and 22, the through holes (half opening parts) may be formed on both the electrodes 21 and 22.

Additionally, although this embodiment illustrates the fluid passage holes 21b and 22b as having cross-sections having designated diameters, the fluid passage holes 21b and 22b formed on the respective electrodes 21 and 22 may have various shapes, including, but not limited to, a shape having a tapered plane, a mortar shape or a bowl shape, i.e., a shape having a diameter decreased or increased from one opening to the other opening.

Further, the fluid passage holes 21b and 22b may have various shapes other than a circle, including, but not limited to, shapes of an oval, a rectangle, a rectilinear slit, a concentric slit, a wave-shaped slit, a crescent moon, a comb, a honeycomb, or a star.

As is apparent from the above description, a deodorization and sterilization apparatus and method in accordance with one embodiment of the present disclosure increases an amount of generated active species and collects floating bacteria or odor materials in air at one place such that the active species contact the collected floating bacteria or odor materials to achieve high-efficiency sterilization and deodorization.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A deodorization and sterilization apparatus, the apparatus comprising:
   a pair of electrodes to carry out plasma discharge and generate an active species by applying a designated voltage between the pair of electrodes, fluid passage holes being disposed at corresponding parts of the pair of electrodes so as to communicate with each other;
   at least one absorption member to absorb floating bacteria or odor materials;
   an air blowing device configured to blow air in a first direction in a first mode and blow air in a second direction in a second mode; and an explosion proof device including protective covers disposed at the outside of the pair of the electrodes to prevent flames generated by the plasma from propagating outside of the protective covers.

2. The deodorization and sterilization apparatus of claim 1, wherein, during the first mode, an air ion number density on a surface of the at least one absorption member or around the surface of the at least one absorption member is approximately $10,000/cm^3$ or more.

3. The deodorization and sterilization apparatus of claim 1, wherein the at least one absorption member includes a plurality of through holes formed in the first direction or the second direction.

4. The deodorization and sterilization apparatus of claim 3, wherein the at least one absorption member includes an absorbent formed of silica gel, activated carbon, zeolite, mesoporous silica, or combinations thereof.

5. The deodorization and sterilization apparatus of claim 4, wherein the at least one absorption member is formed by retaining an absorbent on a mesh base.

6. The deodorization and sterilization apparatus of claim 1, further comprising an ultraviolet lamp, disposed adjacent to the at least one absorption member, used as a subsidiary unit for sterilization and deodorization.

7. The deodorization and sterilization apparatus of claim 1, wherein the at least one absorption member is impregnated with a photocatalyst and an ultraviolet lamp irradiates ultraviolent rays thereto.

8. The deodorization and sterilization apparatus of claim 5, wherein an absorbent is disposed on the protective covers.

9. The deodorization and sterilization apparatus of claim 8, wherein a plurality of absorption members having different absorption characteristics is provided.

10. The deodorization and sterilization apparatus of claim 9, wherein voltage in a pulse mode is applied to the respective electrodes and has a peak value within the range of approximately 100V to 5,000V and a pulse width within the range of approximately 0.1 μs to 300μs.

11. The deodorization and sterilization apparatus of claim 10, wherein DC bias voltage in the range of approximately −500V to +500V is applied to the voltage applied to the respective electrodes.

12. The deodorization and sterilization apparatus of claim 11, further comprising:
a plurality of fluid passage holes corresponding to the pair of electrodes;
a path formation member forming a path to communicate the plurality of fluid passage holes with each other, and air passes through the plurality of communicating fluid passage holes; and
a fluid passage hole among the plurality of fluid passage holes at one end of the path formed by the path formation member faces the upstream in the air blowing direction and another fluid passage hole among the plurality of fluid passage holes at the other end of the path formed by the path formation member faces the at least one absorption member.

13. The deodorization and sterilization apparatus of claim 12, further comprising:
an introduction path formation member to guide the active species generated via the fluid passage holes to the at least one absorption member being disposed between the fluid passage holes and the at least one absorption member,
wherein the introduction path formation member has a retaining structure to retain the active species.

14. The deodorization and sterilization apparatus of claim 13, wherein the deodorization and sterilization apparatus is operable in:
an absorption mode, in which application of voltage to the plasma electrode unit is stopped to allow the at least one absorption member to absorb floating bacteria or odor materials; and
a decomposition mode, in which voltage is applied to the plasma electrode unit after the absorption mode to supply active species generated by plasma to the at least one absorption member.

15. The deodorization and sterilization apparatus of claim 14, further comprising a sensor disposed downstream of the absorption member in the second direction to detect the absorbing capacity of the absorption member and to execute mode switching between the second mode and the first mode, using a result of the detection.

* * * * *